United States Patent
Volz et al.

(10) Patent No.: US 8,557,858 B2
(45) Date of Patent: Oct. 15, 2013

(54) (E)-N-(2-AMINO-PHENYL)-3-{1-[4-(L-METHYL-1H-PYRAZOL-4-YL)-BENZENE-SULFONYL]-1H-PYRROL-3-YL}-ACRYLAMIDE SALTS

(75) Inventors: Jürgen Volz, Radolfzell (DE); Martin Feth, Kelkheim-Hornau (DE); Rolf-Peter Hummel, Radolfzell (DE); Matthias Müller, Constance (DE); Thomas Maier, Stockach (DE); Bernd Müller, Constance (DE)

(73) Assignee: 4SC AG, Planegg-Martinsried (DE)

( * ) Notice: Subject to any disclaimer, the term of this patent is extended or adjusted under 35 U.S.C. 154(b) by 260 days.

(21) Appl. No.: 12/921,889

(22) PCT Filed: Mar. 11, 2009

(86) PCT No.: PCT/EP2009/052859
§ 371 (c)(1), (2), (4) Date: Dec. 7, 2010

(87) PCT Pub. No.: WO2009/112522
PCT Pub. Date: Sep. 17, 2009

(65) Prior Publication Data
US 2011/0086897 A1    Apr. 14, 2011

(30) Foreign Application Priority Data
Mar. 12, 2008  (EP) .................................... 08004568

(51) Int. Cl.
*A61K 31/4155*    (2006.01)
*C07D 231/12*    (2006.01)

(52) U.S. Cl.
USPC ........................................ 514/406; 548/364.1

(58) Field of Classification Search
USPC ........................................ 514/406; 548/364.1
See application file for complete search history.

(56) References Cited

FOREIGN PATENT DOCUMENTS
WO    2006097474 A1    9/2006

OTHER PUBLICATIONS

Berge et al., J. Pharm. Sci. 1977, vol. 66 1-18.*
Neidle, S., Cancer Drug Design and Discovery, ed. (Elsevier/Academic Press, 2008) p. 427-431.*
World Intellectual Property Organization. "International Search Report and Written Opinion." PCT/EP2009/052859. Applicant: 4SC AG. Mailed Jul. 29, 2009.

* cited by examiner

*Primary Examiner* — Jason M Nolan
(74) *Attorney, Agent, or Firm* — Millen, White, Zelano, Branigan, P.C.

(57) ABSTRACT

A salt of (E)-N-{2-amino-phenyl)-3-{1-[4-(1-methyl-1 H-pyrazol-4-yl)-benzenesulfonyl]-1 H-pyrrol-3-yl)-acrylamide selected from the group consisting of the hydrobromide, methansulfonate, hemi ethane-1,2-disulfonate, benzenesulfonate, toiuenesulfonate and 2-naphthalenesulfonate.

13 Claims, 10 Drawing Sheets

# (E)-N-(2-AMINO-PHENYL)-3-{1-[4-(L-METHYL-1H-PYRAZOL-4-YL)-BENZENESULFONYL]-1H-PYRROL-3-YL}-ACRYLAMIDE SALTS

FIELD OF APPLICATION OF THE INVENTION

The invention relates to (E)-N-(2-amino-phenyl)-3-{1-[4-(1-methyl-1H-pyrazol-4-yl)-benzenesulfonyl]-1H-pyrrol-3-yl}-acrylamide salts, which are used in the pharmaceutical industry for the production of pharmaceutical compositions.

TECHNICAL BACKGROUND

Transcriptional regulation in cells is a complex biological process. One basic principle is regulation by posttranslational modification of histone proteins, namely histone proteins H2A/B, H3 and H4 forming the octameric histone core complex. These complex N-terminal modifications at lysine residues by acetylation or methylation and at serine residues by phosphorylation constitute part of the so called "histone code" (Strahl & Ellis, Nature 403, 41-45, 2000). In a simple model, acetylation of positively charged lysine residues decreases affinity to negatively charged DNA, which now becomes accessible for the entry of transcription factors.

Histone acetylation and deacetylation is catalysed by histone acetyltransferases (HATs) and histone deacetylases (HDACs). HDACs are associated with transcriptional repressor complexes, switching chromatin to a transcriptionally inactive, silent structure (Marks et al. Nature Cancer Rev 1, 194-202, 2001). The opposite holds true for HATs which are associated with transcriptional activator complexes. Three different classes of HDACs have been described so far, namely class I (HDAC 1-3, 8) with Mr=42-55 kDa primarily located in the nucleus and sensitive towards inhibition by Trichostatin A (TSA), class II (HDAC 4-7, 9, 10) with Mr=120-130 kDa and TSA sensitivity and class III (Sir2 homologues) which are quite distinct by their $NAD^+$ dependency and TSA insensitivity (Ruijter et al. Biochem. J. 370, 737-749, 2003; Khochbin et al. Curr Opin Gen Dev 11, 162-166, 2001; Verdin et al. Trends Gen 19, 286-293, 2003). HDAC 11 with Mr=39 kDa was cloned recently and displayed homology to class I and II family members (Gao et al. J Biol Chem 277, 25748-25755, 2002). HATs and HDACs exist in large complexes together with transcription factor and platform proteins in cells (Fischle et al. Mol Cell 9, 45-47, 2002). Surprisingly, only about 2% of all genes are regulated by histone acetylation as estimated based on differential display analysis of 340 genes and TSA as the reference HDI (von Lint et al. Gene Expression 5, 245-253, 1996). New studies with SAHA in multiple myeloma cells showed that these transcriptional changes can be grouped into distinct functional gene classes important for e.g. regulation of apoptosis or proliferation (Mitsiades et al. Proc Natl Acad Sci 101, pp 540, 2004).

Substrates different to histone proteins exist. For HDACs these include transcription factors like p53 and TFII E/or chaperones like Hsp90 (Johnstone & Licht, Cancer Cell 4, 13-18, 2003). Therefore the correct name for HDACs would be lysine-specific protein deacetylases. As a consequence of these findings, inhibitors of HDACs effect not only chromatin structure and gene transcription but also protein function and stability by regulating protein acetylation in general. This function of HDACs in protein acetylation might also be important for understanding of immediate gene repression by treatment with HDIs (von Lint et al. Gene Expression 5, 245-253, 1996). In this regard, proteins involved in oncogenic transformation, apoptosis regulation and malignant cell growth are of particular importance.

Different publications highlight the importance of histone acetylation for cancer development (reviewed by Kramer et al. Trends Endocrin Metabol 12, 294-300, 2001; Marks et al. Nature Cancer Rev 1, 194-202, 2001). These diseases include
(i) mutations of the HAT cAMP response element binding protein (CBP) associated with Rubinstein-Taybi syndrome, a cancer predisposition (Murata et al. Hum Mol Genet. 10, 1071-1076, 2001),
(ii) aberrant recruitment of HDAC1 activity by transcription factors in acute promyelocytic leukemia (APL) by the PML-retinoic acid receptor a fusion gene (He et al. Nat genet 18, 126-135, 1998),
(iii) aberrant recruitment of HDAC activity by the overexpressed BCL6 protein in non-Hodgkins lymphoma (Dhordain et al. Nucleic Acid Res 26, 4645-4651, 1998), and finally
(iv) aberrant recruitment of HDAC activity by the AML-ETO fusion protein in acute myelogenous leukemia (AML M2 subtype; Wang et al. Proc Natl Acad Sci USA 95, 10860-10865, 1998). In this AML subtype, the recruitment of HDAC1 activity causally leads to gene silencing, a differentiation block and oncogenic transformation.
(v) HDAC1 gene knock-out in mice showed that HDAC1 has a profound function in embryonal stem cell proliferation by repressing cyclin-dependent kinase inhibitors $p21^{waf1}$ and $p27^{kip1}$ (Lagger et al. Embo J. 21, 2672-2681, 2002). Since $p21^{waf1}$ is induced by HDIs in many cancer cell lines, HDAC1 might be a crucial component in cancer cell proliferation as well. Initial siRNA based gene-knock down experiments in HeLa cells support this hypothesis (Glaser et al. 310, 529-536, 2003).
(vi) HDAC2 is overexpressed in colon carcinoma upon constitutive activation of the wnt/β-catenin/TCF signalling pathay by loss of functional adenomatosis polyposis coli (APC) protein as reported by Zhu et al. recently (Cancer cell 5, 455-463, 2004).

On the molecular level, a plethora of published data with various HDAC inhibitors like Trichostatin A (USA) showed that many cancer relevant genes are up- or down regulated. These include $p21^{waf1}$, Cyclin E, transforming growth factor β (TGFβ), p53 or the von Hippel-Lindau (VHL) tumor suppressor genes, which are upregulated, whereas Bcl-XL, bcl2, hypoxia inducible factor (HIF)1α, vascular endothelial growth factor (VEGF) and cyclin A/D are down-regulated by HDAC inhibition (reviewed by Kramer et al. Trends Endocrin Metabol 12, 294-300, 2001). HDAC inhibitors arrest cells at G1 and G2/M within the cell cycle and deplete S-phase cells, as shown for Depsipeptide as an example (Sandor et al., British J Cancer 83, 817-825, 2000). HDAC inhibitory compounds induce p53 and caspase 3/8 independent apoptosis and have broad anti-tumor activity. Anti-angiogenic activity was described also, which might be related to down-regulation of VEGF and HIF1α. In summary, HDAC inhibition effects tumor cells at different molecular levels and multiple cellular proteins are targeted.

Interestingly, HDAC inhibitors were found to induce cellular differentiation and this pharmacological activity might contribute to their anti-cancer activity as well. For example it was shown recently that suberoylanilide hydroxamic acid (SAHA) induces differentiation of breast cancer cell lines, exemplified by resynthesis of milk fat membrane globule protein (MFMG), milk fat globule protein and lipid (Munster et al. Cancer Res. 61, 8492, 2001).

There is growing rational for synergism of HDAC inhibitors with chemotherapeutic as well as target specific cancer drugs. For example, synergism was shown for SAHA with the kinase/cdk inhibitor flavopiridol (Alemenara et al. Leukemia 16, 1331-1343, 2002), for LAQ-824 with the bcr-abl kinase inhibitor Glivec in CML cells (Nimmanapalli et al. Cancer Res. 63, 5126-5135, 2003), for SAHA and Trichostatin A (TSA) with etoposide (VP16), cisplatin and doxorubicin (Kim et al. Cancer Res. 63, 7291-7300, 2003) and LBH589 with the hsp90 inhibitor 17-allyl-amino-demethoxy-geldanamycin (17-AAG; George et al. Blood online, Oct. 28, 2004). Also it was shown that HDAC inhibition causes reexpression of estrogen or androgen receptors in breast and prostate cancer cells with the potential to resensitize these tumors to anti-hormone therapy (Yang et al. Cancer Res. 60, 6890-6894, 2000; Nakayama et al. Lab Invest 80, 1789-1796, 2000).

HDAC inhibitors from various chemical classes were described in the literature with four most important classes, namely (i) hydroxamic acid analogs, (ii) benzamide analogs, (iii) cyclic peptides/peptolides and (iv) fatty acid analogs. A comprehensive summary of known HDAC inhibitors was published recently by Miller et al. (J Med Chem 46, 5097-5116, 2003). There is only limited data published regarding specificity of these histone deacetylase inhibitors. In general most hydroxamate based HDI are not specific regarding class I and II HDAC enzymes. For example. TSA inhibits HDACs 1, 3, 4, 6 and 10 with $IC_{50}$ values around 20 nM, whereas HDAC8 was inhibited with $IC_{50}$=0.49 μM (Tatamiya et al, AACR Annual Meeting 2004, Abstract #2451). But there are exceptions like the experimental HDI Tubacin, selective for the class II enzyme HDAC 6 (Haggarty et al. Proc nail Acad Sci USA 100, 4389-4394, 2003). In addition, data on class I selectivity of benzamide HDIs are emerging. MS-275 inhibited class I HDAC1 and 3 with $IC_{50}$=0.51 μM and 1.7 μM, respectively. In contrast class II HDACs 4, 6, 8 and 10 were inhibited with $IC_{50}$ values of >100 μM, 82.5 μM and 94.7 μM, respectively (Tatamiya et al, AACR Annual Meeting 2004, Abstract #2451). So far it is not clear if specificity towards HDAC class I or II enzymes or a defined single isoenzyme should be superior regarding therapeutic efficacy and index.

Clinical studies in cancer with HDAC inhibitors are ongoing, namely with SAHA (Merck Inc.), Valproic acid, FK228/Depsipeptide (Gloucester Pharmaceuticals/NCI), MS275 (Berlex-Schering), NVP LBH-589 (Novartis), PXD-101 (Topotarget/Curagen), MGCD0103 (Methylgene Inc) and Pivaloyloxymethylbutyrate/Pivanex (Titan Pharmaceuticals). These studies showed first evidence of clinical efficacy, highlighted recently by partial and complete responses with FK228/Depsipeptide in patients with peripheral T-cell lymphoma (Plekarz et al. Blood, 98, 2865-2868, 2001) and diffuse large B-cell lymphoma by SAHA (Kelly et al. J. Clin. Oncol. 23, 3923-3931, 2005).

Recent publications also showed possible medical use of HDAC inhibitors in diseases different to cancer. These diseases include systemic lupus erythematosus (Mishra et al. J Clin Invest 111, 539-552, 2003, Reilly et al. J. Immunol. 173, 4171-4178, 2004), rheumatoid arthritis (Chung et al. Mol Therapy 8, 707-717, 2003; Nishida et al. Arthritis & Rheumatology 50, 3365-3376, 2004), inflammatory diseases (Leoni et al. Proc Natl Acad Sci USA 99, 2995-3000, 2002) and neurodegenerative diseases like Huntington's disease (Steffan et al. Nature 413, 739-743, 2001, Hockly et al. Proc Natl Acad Sci USA 100(4):2041-6, 2003).

Cancer chemotherapy was established based on the concept that cancer cells with uncontrolled proliferation and a high proportion of cells in mitosis are killed preferentially. Standard cancer chemotherapeutic drugs finally kill cancer cells upon induction of programmed cell death ("apoptosis") by targeting basic cellular processes and molecules, namely RNA/DNA (alkylating and carbamylating agents, platin analogs and topoisomerase inhibitors), metabolism (drugs of this class are named anti-metabolites) as well as the mitotic spindle apparatus (stabilizing and destabilizing tubulin inhibitors). Inhibitors of histone deacetylases (HDIs) constitute a new class of anti cancer drugs with differentiation and apoptosis inducing activity. By targeting histone deacetylases, HDIs effect histone (protein) acetylation and chromatin structure, inducing a complex transcriptional reprogramming, exemplified by reactivation of tumor suppressor genes and repression of oncogenes. Beside effecting acetylation of N-terminal lysine residues in core histone proteins, non-histone targets important for cancer cell biology like heat-shock-protein 90 (Hsp90) or the p53 tumor suppressor protein exist. The medical use of HDIs might not be restricted to cancer therapy, since efficacy in models for inflammatory diseases, rheumatoid arthritis and neurodegeneration was shown.

Benzoyl or acetyl substituted pyrrolyl propenamides are described in the public literature as HDAC-inhibitors, whereas the connectivity of the acyl-group is at position 2 or 3 of the pyrrole scaffold. (Mai et. al., Journal Med. Chem. 2004, Vol. 47, No. 5, 1098-1109; or Ragno et al., Journal Med. Chem. 2004, Vol. 47, No. 5, 1351-1359). Further pyrrolyl substituted hydroxamic acid derivatives are described in U.S. Pat. No. 4,960,787 as lipoxygenase inhibitors or in U.S. Pat. No. 6,432,999 as cyclooxygenase inhibitors.

Various compounds, which are said to be HDAC inhibitors, are reported in WO 01/38322; Journal Med. Chem. 2003, Vol. 46, No. 24, 5097-5116; Journal Med. Chem. 2003, Vol. 46, No. 4, 512-524; Journal Med. Chem. 2003, Vol. 46, No. 5, 820-830; and in Current Opinion Drug Discovery 2002, Vol. 5, 487-499.

Addressing the remaining need in the art for new, well-tolerated and more efficacious inhibitors of HDACs, WO 2006/097474 describes novel N-sulphonylpyrrole derivatives, which differ profoundly from prior art compounds and are effective inhibitors of histone deacetylases having surprising and particularly advantageous properties.

Among them the hydrochloride salt of (E)-N-(2-amino-phenyl)-3-{1-[4-(1-methyl-1H-pyrazol-4-yl)-benzenesulfonyl]-1H-pyrrol-3-yl}-acrylamide is exemplified.

However, compounds disclosed in WO 2006/097474 still suffer from a relatively low solubility and/or high hygroscopicity.

DESCRIPTION OF THE INVENTION

In accordance with a first aspect of the present invention, new salts of (E)-N-(2-amino-phenyl)-3-{1-[4-(1-methyl-1H-pyrazol-4-yl)-benzenesulfonyl]-1H-pyrrol-3-yl}-acrylamide have now been synthesized, which are described in more detail below and surprisingly show a superior dissolution behavior than the free base and have a higher stability than the hydrochloride salt of (E)-N-(2-amino-phenyl)-3-{1-[4-(1-methyl-1H-pyrazol-4-yl)-benzenesulfonyl]-1H-pyrrol-3-yl}-acrylamide as disclosed in WO 2006/097474. These salts display different polymorphic forms, which may also result in a better bioavailability of the drug substance.

The present invention thus relates in a first general aspect to certain salts of (E)-N-(2-amino-phenyl)-3-{1-[4-(1-methyl-1H-pyrazol-4-yl)-benzenesulfonyl]-1H-pyrrol-3-yl}-acrylamide that are characterized by an improved dissolution behavior and a lower hygroscopicity, when compared to the known hydrochloride salt.

In a further aspect the present invention relates to salts of (E)-N-(2-amino-phenyl)-3-{1-[4-(1-methyl-1H-pyrazol-4-yl)-benzenesulfonyl]-1H-pyrrol-3-yl}-acrylamide, selected from the group consisting of hydrobromide, methansulfonate, hemi ethane-1,2-disulfonate, benzenesulfonate, toluenesulfonate and 2-naphthalenesulfonate.

A particularly preferred aspect of the present invention is the toluenesulfonate salt of (E)-N-(2-amino-phenyl)-3-{1 [4-(1-methyl-1H-pyrazol-4-yl)-benzenesulfonyl]-1H-pyrrol-3-yl}acrylamide. It was unexpectedly found that this salt has a particularly high dissolution velocity, in addition to a high solubility, as well as an enhanced stability, when compared to the known hydrochloride salt, and thus is expected to show superior pharmacokinetic properties in vivo.

In a third aspect the present invention relates to certain polymorphs of the hydrobromide, the methansulfonate, the hemi ethane-1,2-disulfonate, the benzenesulfonate, the toluenesulfonate and the 2-naphthalenesulfonate salt, respectively, of the (E)-N-(2-amino-phenyl)-3-{1-[4-(1-methyl-1H-pyrazol-4-yl)-benzenesulfonyl]-1H-pyrrol-3-yl}-acrylamide, which are characterized by their respective powder X-ray diffractograms and in particular by the main peaks of their respective powder X-ray diffractograms.

BEST MODE FOR CARRYING OUT THE INVENTION

Figure 1:
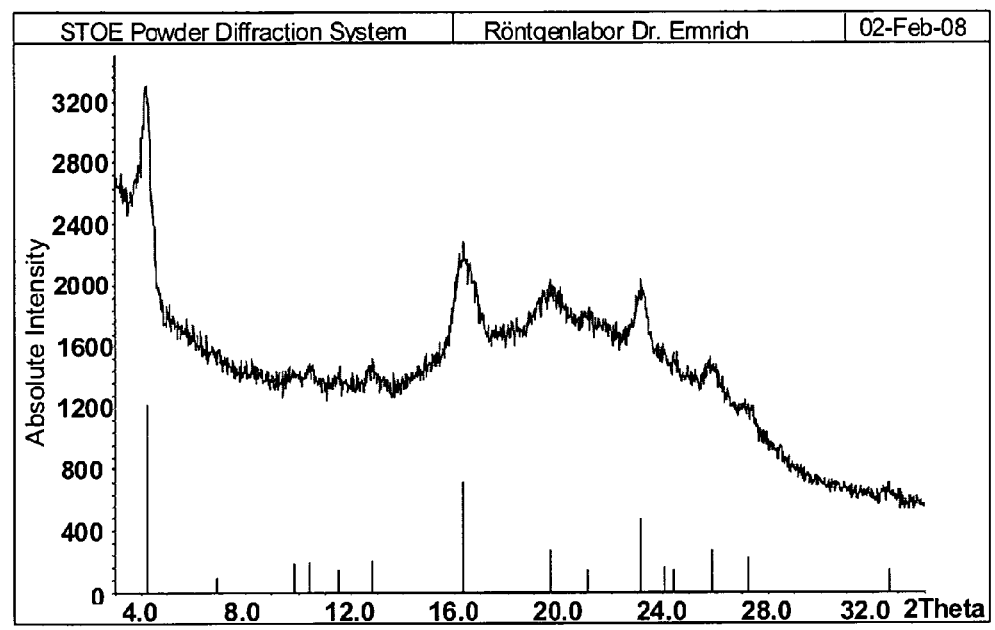
FIG. 1: XRPD pattern of partially amorphous (E)-N-(2-amino-phenyl)-3-{1-[4-(1-methyl-1H-pyrazol-4-yl)-benzenesulfonyl]-1H-pyrrol-3-yl}-acrylamide

The salts of (E)-N-(2-amino-phenyl)-3-{1-[(4-(1-methyl-1H-pyrazol-4-yl)-benzenesulfonyl]-1H-pyrrol-3-yl}-acrylamide according to the invention can be obtained by dissolving the free base of this compound in a suitable solvent (e.g. a ketone, such as acetone, methyl ethyl ketone or methyl isobutyl ketone, an ether, such as diethyl ether, tetrahydrofuran or dioxane, a chlorinated hydrocarbon, such as methylene chloride or chloroform, or a low molecular weight aliphatic alcohol such as methanol, ethanol or isopropanol) which contains the desired acid, or to which the desired acid is then added. The salts are obtained by filtering, reprecipitating, precipitating with a nonsolvent for the addition salt or by evaporating the solvent. Salts obtained can be converted by alkalization or by acidification into the free compound, which in turn can be converted into further salts. In this way, pharmacologically intolerable salts can be converted into pharmacologically tolerable salts.

Depending on the reaction conditions used, the amount of the respective acid anion contained in the salts may lie in the range from about 0.1 to about 5 mol equivalents of the free base, more precisely from about 0.3 to about 3 mol equivalents, more precisely from about 0.6 to about 2.4 mol equivalents, determined according to art-known procedures, e.g. titration or NMR-methods.

Crystalline salts of (E)-N-(2-amino-phenyl)-3-{1-[4-(1-methyl-1H-pyrazol-4-yl)-benzenesulfonyl]-1H-pyrrol-3-yl}-acrylamide can be obtained by a process comprising the step of crystallization or recrystallization of any form or mixtures of any forms with acid in a solution comprising an organic solvent (e.g. an alcohol like methanol or ethanol, or a ketone like acetone) or a mixture of organic solvents, or mixtures thereof with water, or only water.

Polymorphs can be obtained by a number of methods known in the art. Such methods include, without being restricted to, solvent (re)crystallization, precipitating with a non-solvent, rapid evaporation, slow evaporation, rapid cooling, slow cooling and the like. Solvates or particularly the hydrates of the salts according to this invention can be prepared in a manner known per se, e.g. in the presence of the appropriate solvent. Hydrates may be obtained from water or from mixtures of water with polar organic solvents (for example alcohols, e.g. methanol, ethanol or isopropanol, or ketones, e.g. acetone). The salts according to the present invention include each and every solvate and hydrate that can be formed therewith, and each and every crystalline semi-crystalline or amorphous form. Crystalline forms are generally preferred.

The following examples serve to illustrate the invention further without restricting it.

EXAMPLES

The XRPD (X-ray powder diffraction) measurements given in the following are performed in transmission (U=40 kV, I=30 mA, Cu—Kα).

(E)-N-(2-Amino-phenyl)-3-{1-[4-(1-methyl-1H-pyrazol-4-yl-benzenesulfonyl]-1H-pyrrol-3-yl}-acrylamide Partially Amorphous 3.82 g (E)-N-(2-Amino-phenyl)-3-{1-[(4-(1-methyl-1H-pyrazol-4-yl)-benzenesulfonyl]-1H-pyrrol-3-yl}-acrylamide dihydrochloride was suspended in 38 mL water and 2.7 mL aq. ammonia solution (25%) was added. The suspension was stirred for 1 h and filtered. The filter cake was washed with 19 mL water and dried. An off-white solid (3.09 g) was obtained.

The characteristic peaks of the X-ray powder diffraction pattern of this salt are substantially summarized in Table 1 and substantially shown in FIG. 1.

TABLE 1

XRPD pattern of partially amorphous (E)-N-(2-amino-phenyl)-3-{1-[4-(1-methyl-1H-pyrazol-4-yl)-benzenesulfonyl]-1H-pyrrol-3-yl}-acrylamide comprising the following peaks (relative intensities >10)

| 2Theta | I(rel) |
|---|---|
| 4.2 | 100.0 |
| 9.9 | 15.0 |
| 10.5 | 15.6 |
| 11.5 | 11.2 |
| 12.8 | 16.6 |
| 16.3 | 58.5 |
| 19.7 | 21.9 |
| 21.1 | 11.3 |
| 23.2 | 38.5 |
| 24.1 | 12.6 |
| 24.5 | 11.2 |
| 25.9 | 21.9 |
| 27.3 | 18.2 |
| 32.6 | 11.2 |

Crystalline Polymorph A 10.0 g of (E)-N-(2-amino-phenyl)-3-{1-[4-(1-methyl-1H-pyrazol-4-yl)-benzenesulfonyl]-1H-pyrrol-3-yl}-acrylamide dihydrochloride (19.2 mmol) was treated with a mixture of 300 ml THF and 375 ml of an aqueous $Na_2CO_3$-solution (8%). The aqueous phase was separated and extracted with 100 ml THF. The combined organic phases were treated with 235 ml water and the organic part of the mixture is evaporated. By this, the free bases separate as brownish solid. The aqueous solution was dekanted off, and the residue was dissolved in 120 ml THF, adsorbed on 100 g silicagel-60 (Merck) and chromatographed with 470 g silicagel-60 (Merck). The compound was eluted with $CHCl_3$/MeOH (20:1). The product containing fractions were carefully evaporated. 6.00 g of a colorless solid were obtained.

Figure 2:
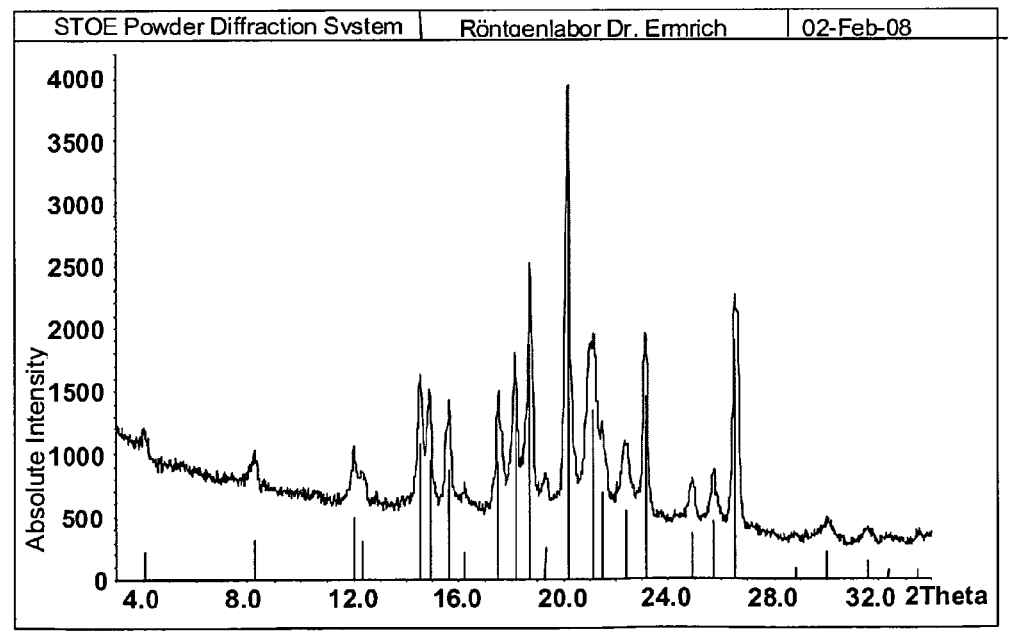
FIG. 2: XRPD pattern of crystalline (E)-N-(2-amino-phenyl)-3-{1-[4-(1-methyl-1H-pyrazol-4-yl)-benzenesulfonyl]-1H-pyrrol-3-yl}-acrylamide polymorph A

The characteristic peaks of the X-ray powder diffraction pattern of this salt are substantially summarized in Table 2 and substantially shown in FIG. 2.

TABLE 2

XRPD pattern of crystalline (E)-N-(2-amino-phenyl)-3-{1-[4-(1-methyl-1H-pyrazol-4-yl)-benzenesulfonyl]-1H-pyrrol-3-yl}-acrylamide polymorph A comprising the following peaks (relative intensities >10)

| 2Theta | I(rel) |
|---|---|
| 12.0 | 14.9 |
| 14.5 | 32.4 |
| 14.9 | 28.4 |
| 15.6 | 26.2 |
| 17.5 | 28.1 |
| 18.1 | 36.8 |
| 18.7 | 56.3 |
| 20.2 | 100.0 |
| 21.1 | 40.7 |
| 21.5 | 20.6 |
| 22.4 | 16.4 |
| 23.1 | 43.7 |
| 24.9 | 11.0 |
| 25.7 | 13.7 |
| 26.5 | 57.0 |

Crystalline Polymorph B 20.0 g (E)-N-(2-Amino-phenyl)-3-{1-[4-(1-methyl-1H-pyrazol-4-yl)-benzenesulfonyl]-1H-pyrrol-3-yl}-acrylamide dihydrochloride was suspended in 200 mL water and 100 mL ethanol. 8.7 mL aq. ammonia solution (25%) was added and the suspension was stirred for 1 h. The suspension was filtered; the filter cake was washed with 100 mL water and dried. An off-white solid (16.4 g) was obtained. The solid (10.0 g) was suspended in 200 mL ethanol and refluxed for 10 min. After cooling to room temperature the suspension was filtered and dried. An off-white solid (8.8 g) was obtained.

Figure 3:
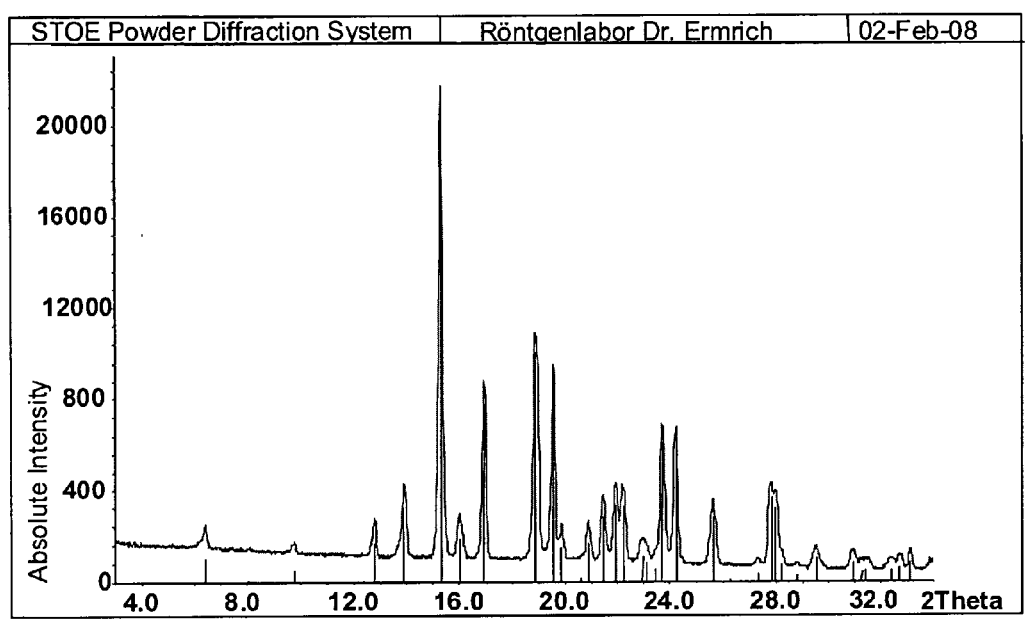
FIG. 3: XRPD pattern of crystalline (E)-N-(2-amino-phenyl)-3-{1-[4-(1-methyl-1H-pyrazol-4-yl)benzenesulfonyl]-1H-pyrrol-3-yl}-acrylamide polymorph B

The characteristic peaks of the X-ray powder diffraction pattern of this salt are substantially summarized in Table 3 and substantially shown in FIG. 3.

TABLE 3

XRPD pattern of crystalline (E)-N-(2-amino-phenyl)-3-{1-[4-(1-methyl-1H-pyrazol-4-yl)-benzenesulfonyl]-1H-pyrrol-3-yl}-acrylamide polymorph B comprising the following peaks (relative intensities >10)

| 2Theta | I(rel) |
|---|---|
| 13.9 | 15.7 |
| 15.3 | 100.0 |
| 16.9 | 37.7 |
| 18.9 | 48.6 |
| 19.8 | 41.3 |
| 21.5 | 13.6 |
| 21.9 | 16.3 |
| 22.2 | 15.9 |
| 23.7 | 29.3 |
| 24.2 | 28.3 |
| 25.6 | 13.5 |
| 27.8 | 17.9 |
| 28.0 | 15.5 |

(E)-N-(2-Amino-phenyl)-3-{1-[4-(1-methyl-1H-pyrazol-4-yl)-benzenesulfonyl]-1H-pyrrol-3-yl}-acrylamide monohydrochloride To 225 mg (E)-N-(2-amino-phenyl)-3-{1-[4-(1-methyl-1H-pyrazol-4-yl)-benzenesulfonyl]-1H-pyrrol-3-yl}-acrylamide (0.50 mmol) in 20 ml of warm methanol a solution (3.13 mL, 0.5 mmol) of HCl in methanol (to 4 mL 4N $HCl_{aqueous}$ methanol was added to a final of 100 mL=0.16 mmol/mL) was added dropwise. Immediately, a yellowish oil separated. By adding diethyl ether (10 mL) the full separation was done. The resulting solid was dried overnight. Yield: 248 mg (102%); yellowish solid; MP: 150-164° C., sinter. The compound contained 0.91 HCl/Mol.

Figure 4:
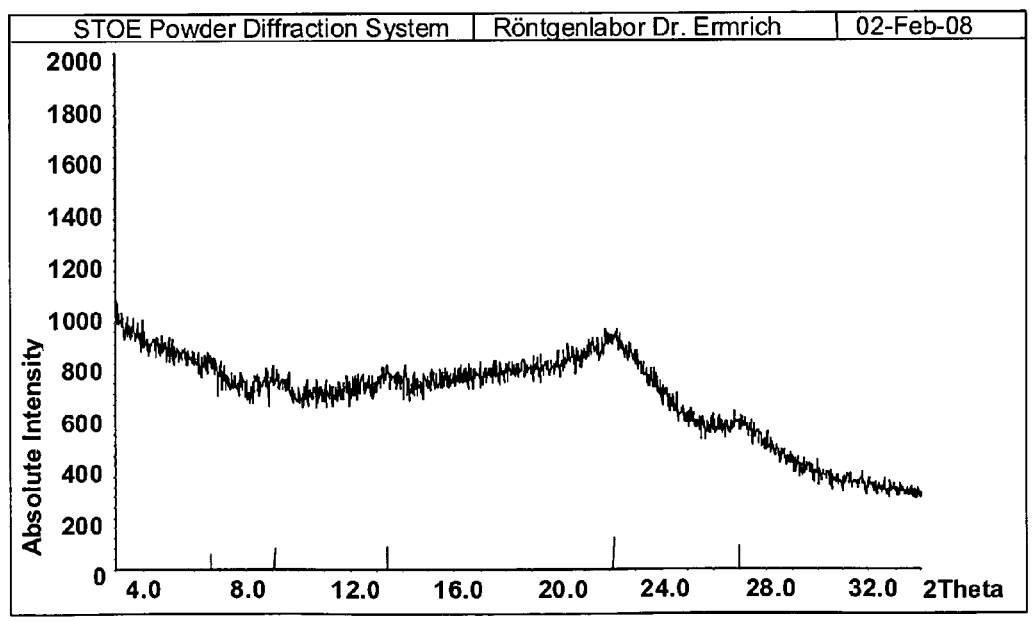
FIG. 4: XRPD pattern of (E)-N-(2-amino-phenyl)-3-{1-[4-(1-methyl-1H-pyrazol-4-yl)-benzenesulfonyl]-1H-pyrrol-3-yl}-acrylamide monohydrochloride

The characteristic peaks of the X-ray powder diffraction pattern of this salt are substantially summarized in Table 4 and substantially shown in FIG. 4.

TABLE 4

XRPD pattern of (E)-N-(2-amino-phenyl)-3-{1-[4-(1-methyl-1H-pyrazol-4-yl)-benzenesulfonyl]-1H-pyrrol-3-yl}-acrylamide monohydrochloride comprising the following peaks (relative intensities >10)

| 2Theta | I(rel) |
| --- | --- |
| 6.7 | 47.4 |
| 9.1 | 65.0 |
| 13.4 | 70.1 |
| 22.2 | 100.0 |
| 27.0 | 72.2 |

(E)-N-(2-Amino-phenyl)-3-{1-[4-(1-methyl-1H-pyrazol-4-yl)-benzenesulfonyl]-1H-pyrrol-3-yl}-acrylamide dihydrochloride 5.0 g [2-((E)-3-{1-[4-(1-Methyl-1H-pyrazol-4-yl)-benzenesulfonyl]-pyrrol-3-yl}-acryloylamino)-phenyl]-carbamic acid tert-butyl ester was suspended in 90 mL THF and 7.5 mL water. 7.5 mL aq. hydrochloric acid (37%) was added and the suspension was stirred at 60° C. for 4 h. After cooling to room temperature the suspension was filtered, the filter cake was washed with 20 mL THF and dried. An off-white solid (3.7 g) was obtained. The compound contained 1.82 HCl/Mol.

Figure 5:
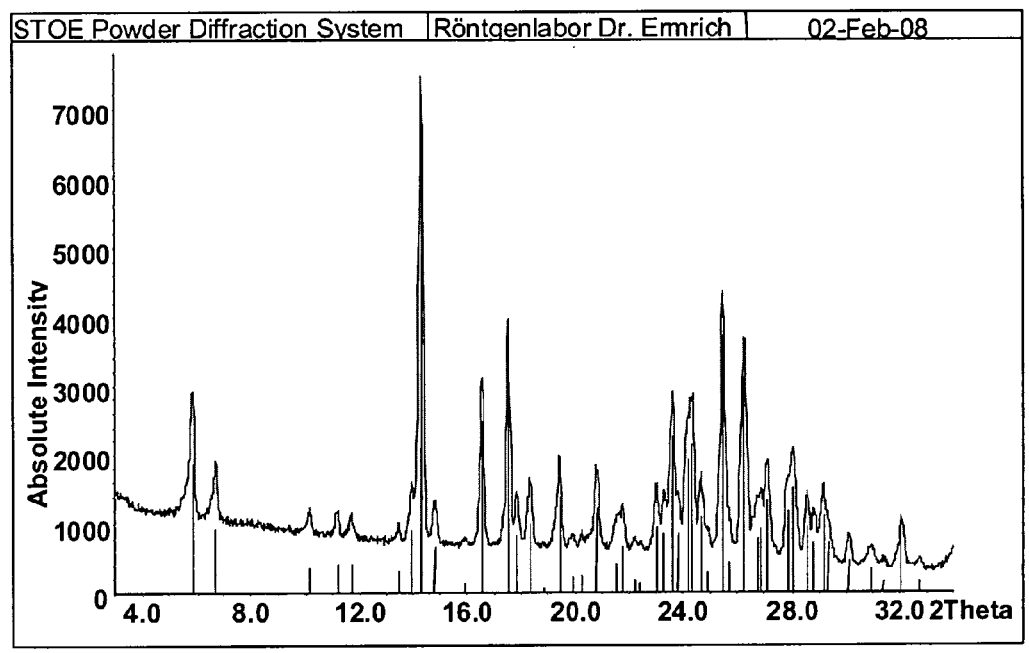
FIG. 5: XRPD pattern of crystalline (E)-N-(2-amino-phenyl)-3-{1-[4-(1-methyl-1H-pyrazol-4-yl)-benzenesulfonyl]-1H-pyrrol-3-yl}-acrylamide dihydrochloride

The characteristic peaks of the X-ray powder diffraction pattern of this salt are substantially summarized in Table 5 and substantially shown in FIG. 5.

TABLE 5

XRPD pattern of crystalline (E)-N-(2-amino-phenyl)-3-{1-[4-(1-methyl-1H-pyrazol-4-yl)-benzenesulfonyl]-1H-pyrrol-3-yl}-acrylamide dihydrochloride comprising the following peaks (relative intensities >10)

| 2Theta | I(rel) |
| --- | --- |
| 5.8 | 27.6 |
| 6.7 | 13.7 |
| 13.9 | 13.3 |
| 14.3 | 100.0 |
| 16.5 | 36.6 |
| 17.5 | 48.9 |
| 17.8 | 12.2 |
| 18.3 | 14.7 |
| 19.4 | 20.1 |
| 20.8 | 17.9 |
| 23.0 | 13.9 |
| 23.3 | 12.6 |
| 23.6 | 33.4 |
| 23.8 | 12.6 |
| 24.2 | 28.5 |
| 24.3 | 31.4 |
| 24.7 | 16.0 |
| 25.5 | 55.1 |
| 26.2 | 46.0 |
| 26.7 | 11.8 |
| 26.9 | 13.8 |
| 27.1 | 19.7 |
| 27.8 | 17.2 |
| 28.0 | 22.3 |
| 28.5 | 14.1 |
| 28.8 | 10.6 |
| 29.1 | 16.2 |
| 29.3 | 10.6 |
| 32.0 | 11.1 |

(E)-N-(2-Amino-phenyl)-3-{1-[4-(1-methyl-1H-pyrazol-4-yl)-benzenesulfonyl]-1H-pyrrol-3-yl}-acrylamide hydrobromide To 0.21 g of (E)-N-(2-amino-phenyl)-3-{1-[4-(1-methyl-1H-pyrazol-4-yl)-benzenesulfonyl]-1H-pyrrol-3-yl}-acrylamide in 4 ml THF a solution of 0.169 ml of 48%-HBr (169 µL, 1.5 mmol) in 4 ml THF was added dropwise. A solid separated, which was treated with diethylether. The resulting crystalline solid was separated and dried overnight. Yield: 287 mg (100%); MP: 200° C., sinter. The compound contained 1.86 HBr/Mol.

(E)-N-(2-Amino-phenyl)-3-{1-[4-(1-methyl-1H-pyrazol-4-A-benzenesulfonyl]-1H-pyrrol-3-yl}-acrylamide methansulfonate Partially Amorphous 500 mg of (E)-N-(2-amino-phenyl)-3-{1-[4-(1-methyl-1H-pyrazol-4-yl)-benzenesulfonyl]-1H-pyrrol-3-yl}-acrylamide, 10 ml of water and 1 ml methanol were heated to 130° C. 0.435 ml methanesulfonic acid was added. The mixture was nearly dissolved. The mixture was then immediately cooled in an ice bath. During cooling, a brownish solid separated. The mixture was treated with ultrasonic. Subsequently, the resulting solid was collected and dried. The molar ratio of free base to methanesulfonic acid was 1:0.95.

Figure 6:
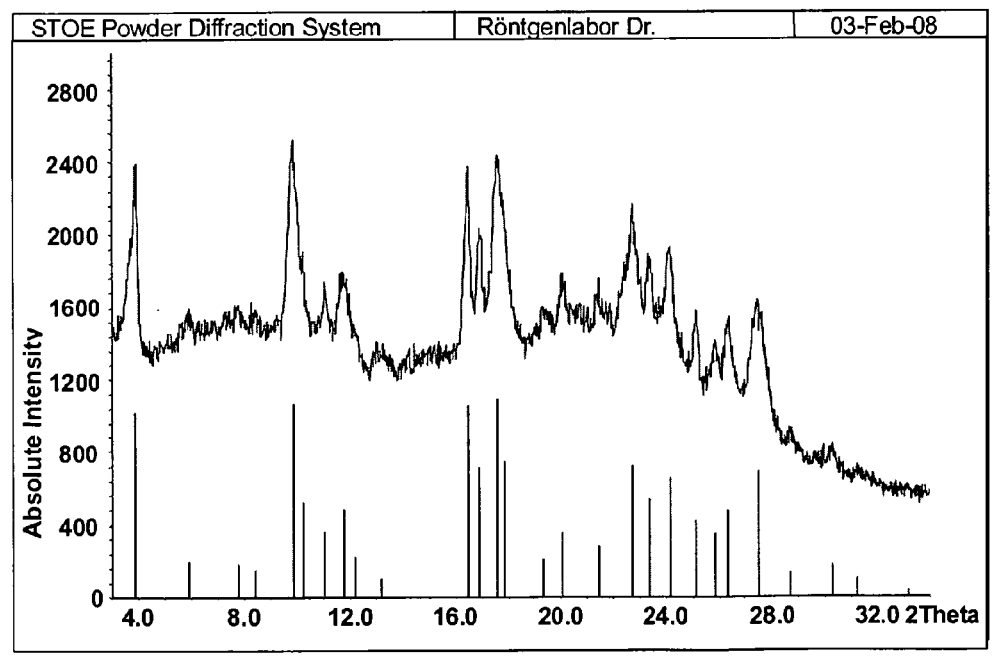
FIG. 6: XRPD pattern of partially amorphous (E)-N-(2-amino-phenyl)-3-{1-[4-(1-methyl-1H-pyrazol-4-yl)-benzenesulfonyl]-1H-pyrrol-3-yl}-acrylamide methansulfonate

The characteristic peaks of the X-ray powder diffraction pattern of this salt are substantially summarized in Table 6 and substantially shown in FIG. 6.

TABLE 6

XRPD pattern of partially amorphous (E)-N-(2-amino-phenyl)-3-{1-[4-(1-methyl-1H-pyrazol-4-yl)-benzenesulfonyl]-1H-pyrrol-3-yl}-acrylamide methansulfonate comprising the following peaks (relative intensities >10)

| 2Theta | I(rel) |
| --- | --- |
| 3.9 | 93.9 |
| 5.9 | 18.8 |
| 7.8 | 16.5 |
| 8.4 | 13.3 |
| 9.8 | 98.1 |
| 10.2 | 47.6 |
| 11.1 | 33.4 |

TABLE 6-continued

XRPD pattern of partially amorphous (E)-N-(2-amino-phenyl)-3-
{1-[4-(1-methyl-1H-pyrazol-4-yl)-benzenesulfonyl]-1H-pyrrol-3-yl}-
acrylamide methansulfonate comprising the following peaks
(relative intensities >10)

| 2Theta | I(rel) |
|---|---|
| 11.7 | 44.2 |
| 12.2 | 19.8 |
| 16.5 | 97.3 |
| 16.9 | 65.1 |
| 17.6 | 100.0 |
| 17.9 | 68.2 |
| 19.3 | 19.3 |
| 20.1 | 32.9 |
| 21.5 | 25.4 |
| 22.7 | 65.6 |
| 23.4 | 49.1 |
| 24.1 | 60.6 |
| 25.1 | 38.4 |
| 25.9 | 31.6 |
| 26.39 | 43.5 |
| 27.5 | 63.5 |
| 28.7 | 12.1 |
| 30.3 | 15.9 |

Cystalline 250 mg of (E)-N-(2-amino-phenyl)-3-{1-[4-(1-methyl-1H-pyrazol-4-yl)-benzenesulfonyl]-1H-pyrrol-3-yl}-acrylamide, 5 ml water, 0.5 ml methanol and 0.112 ml methanesulfonic acid were heated to 130° C. for 10 min. After stirring at ambient temperature overnight the solid was collected and dried. The molar ratio of free base to methanesulfonic acid was 1:0.66.

Figure 7:
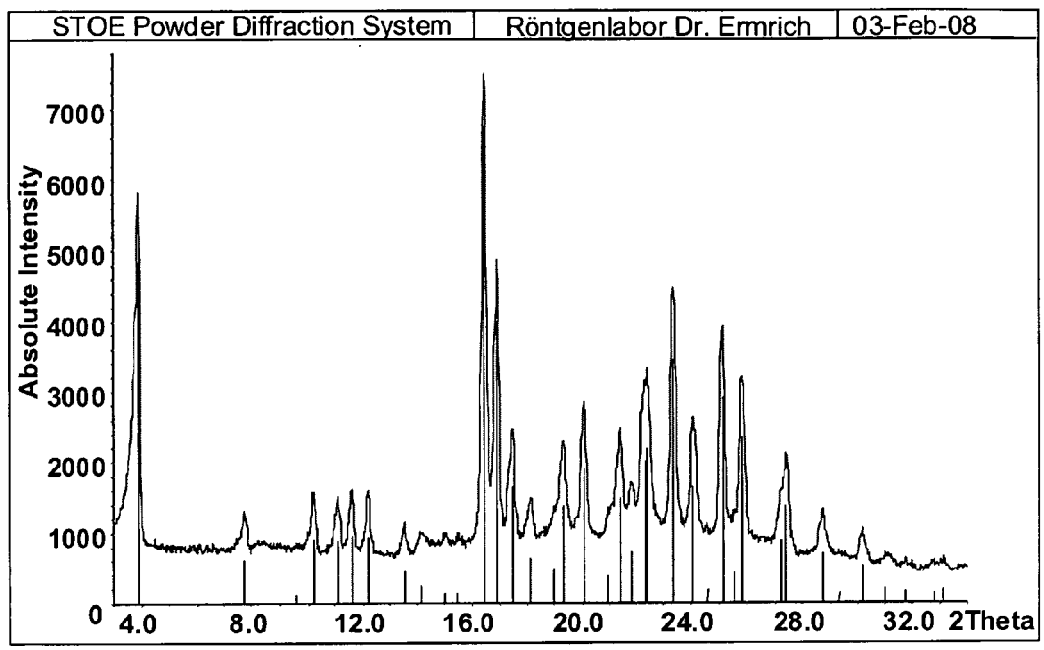
FIG. 7: XRPD pattern of crystalline (E)-N-(2-amino-phenyl)-3-{1-[4-(1-methyl-1H-pyrazol-4-yl)-benzenesulfonyl]-1H-pyrrol-3-yl}-acrylamide methansulfonate

The characteristic peaks of the X-ray powder diffraction pattern of this salt are substantially summarized in Table 7 and substantially shown in FIG. 7.

TABLE 7

XRPD pattern of crystalline (E)-N-(2-amino-phenyl)-3-{1-[4-(1-
methyl-1H-pyrazol-4-yl)-benzenesulfonyl]-1H-pyrrol-3-yl}-acrylamide
methansulfonate comprising the following peaks (relative intensities > 10)

| 2Theta | I(rel) |
|---|---|
| 3.9 | 72.0 |
| 10.2 | 13.2 |
| 11.1 | 12.9 |
| 11.6 | 14.2 |
| 12.2 | 13.7 |
| 16.4 | 100.0 |
| 16.9 | 59.1 |
| 17.4 | 24.5 |
| 19.3 | 20.2 |
| 20.1 | 27.9 |
| 21.4 | 22.1 |
| 21.8 | 10.8 |
| 22.3 | 30.0 |
| 22.4 | 32.6 |
| 23.3 | 51.4 |
| 24.1 | 24.3 |
| 25.1 | 43.1 |
| 25.8 | 34.7 |
| 27.2 | 12.9 |
| 27.4 | 20.1 |
| 28.7 | 10.4 |

(E)-N-(2-Amino-phenyl-3-{1-[4-(1-methyl-1H-pyrazol-4-yl-benzenesulfonyl]-1H-pyrrol-3-yl}-acrylamide hemi ethane-1,2-sulfonate 1.00 g (E)-N-(2-Amino-phenyl)-3-{1-[4-(1-methyl-1H-pyrazol-4-yl)-benzene sulfonyl]-1H-pyrrol-3-yl}-acrylamide was suspended in 20 water. 512 mg ethanedisulfonic acid hydrate in 5 ml water was added and the suspension was stirred for 18 h. The suspension was filtered and dried. An off-white solid (1.09 g) was obtained. The molar ratio of free base to ethanesulfonic acid was 1:0.5

Figure 8:
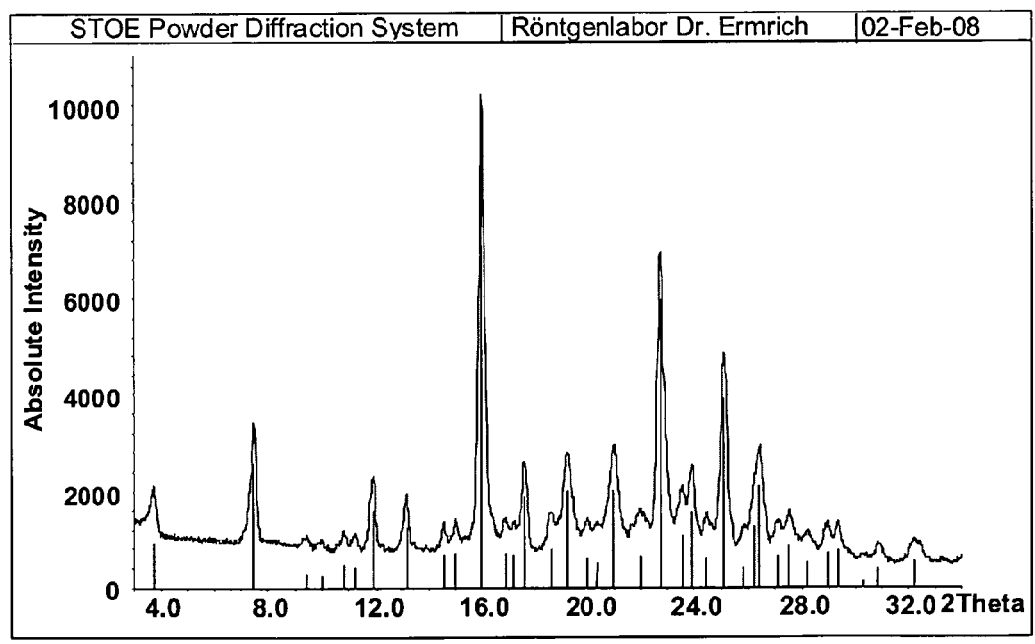
FIG. 8: XRPD pattern of (E)-N-(2-amino-phenyl)-3-{1-[4-(1-methyl-1H-pyrazol-4-yl)-benzenesulfonyl]-1H-pyrrol-3-yl}-acrylamide hemi ethane-1,2-sulfonate

The characteristic peaks of the X-ray powder diffraction pattern of this salt are substantially summarized in Table 8 and substantially shown in FIG. 8.

TABLE 8

XRPD pattern (E)-N-(2-amino-phenyl)-3-{1-[4-(1-methyl-1H-
pyrazol-4-yl)-benzenesulfonyl]-1H-pyrrol-3-yl}-acrylamide hemi ethane-
1,2-sulfonate comprising the following peaks (relative intensities > 10)

| 2Theta | I(rel) |
|---|---|
| 7.5 | 27.2 |
| 11.9 | 16.7 |
| 13.1 | 12.8 |
| 16.0 | 100.0 |
| 17.6 | 19.8 |
| 19.2 | 20.9 |
| 21.0 | 21.0 |
| 22.7 | 63.5 |
| 23.5 | 11.2 |
| 23.9 | 16.3 |
| 25.1 | 41.2 |
| 26.2 | 13.3 |
| 26.4 | 22.0 |

(E)-N-(2-Amino-phenyl)-3-{1-[4-(1-methyl-1H-pyrazol-4-yl)-benzenesulfonyl]-1H-pyrrol-3-yl}-acrylamide benzenesulfonate 1.65 g (E)-N-(2-Amino-phenyl)-3-{1-[4-(1-methyl-1H-pyrazol-4-yl)-benzene sulfonyl]-1H-pyrrol-3-yl}-acrylamide was suspended in 30 mL water and 642 mg benzenesulfonic acid was added. The suspension was stirred for 26 h, filtered and dried. An off-white solid (2.04 g) was obtained. The molar ratio of free base to benzenesulfonic acid was 1:0.99.

Figure 9:
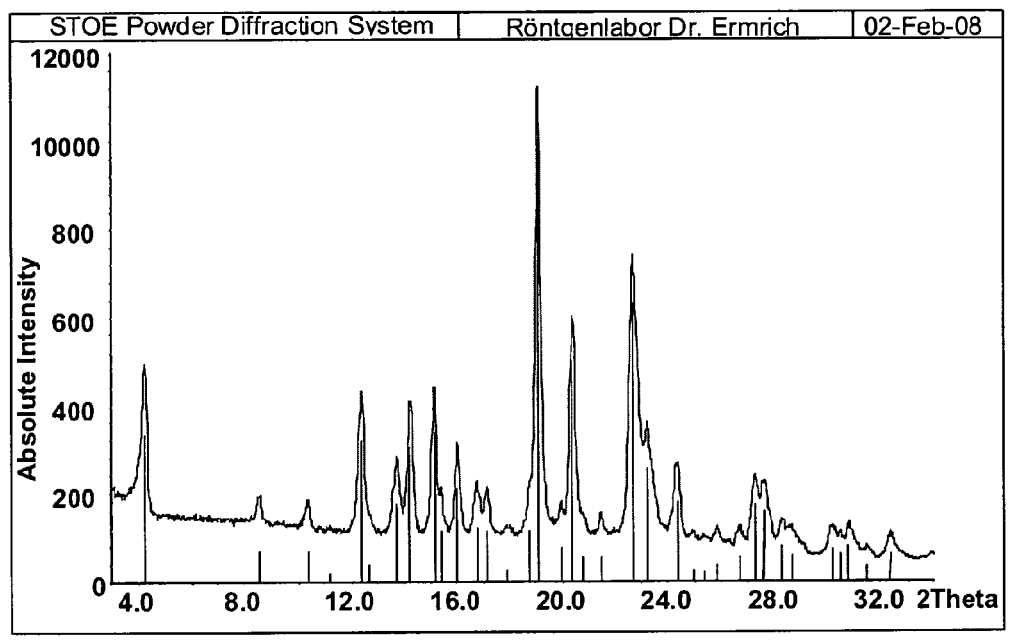
FIG. 9: XRPD pattern of (E)-N-(2-amino-phenyl)-3-{1-[4-(1-methyl-1H-pyrazol-4-yl)-benzenesulfonyl]-1H-pyrrol-3-yl}-acrylamide benzenesulfonate

The characteristic peaks of the X-ray powder diffraction pattern of this salt are substantially summarized in Table 9 and substantially shown in FIG. 9.

TABLE 9

XRPD pattern of (E)-N-(2-amino-phenyl)-3-{1-[4-(1-methyl-1H-
pyrazol-4-yl)-benzenesulfonyl]-1H-pyrrol-3-yl}-acrylamide
benzenesulfonate comprising the following peaks (relative intensities > 10)

| 2Theta | I(rel) |
|---|---|
| 4.3 | 33.2 |
| 12.4 | 31.7 |
| 13.7 | 17.7 |
| 14.2 | 30.6 |
| 15.1 | 33.8 |
| 15.4 | 11.3 |
| 16.0 | 20.8 |
| 16.7 | 12.2 |
| 17.1 | 11.4 |
| 18.7 | 11.4 |
| 19.1 | 100.0 |
| 20.4 | 49.9 |
| 22.7 | 63.1 |
| 23.2 | 25.4 |
| 24.3 | 17.7 |
| 27.3 | 17.1 |
| 27.6 | 15.8 |

(E)-N-(2-Amino-phenyl)-3-{1-[4-(1-methyl-1H-pyrazol-4-yl)-benzenesulfonyl]-H-pyrrol-3-yl}-acrylamide toluene-4-sulfonate Crystalline Polymorph A 5.0 g (E)-N-(2-Amino-phenyl)-3-{1-[4-(1-methyl-1H-pyrazol-4-yl)-benzenesulfonyl]-1H-pyrrol-3-yl}-acrylamide was suspended in 150 mL methanol and 2.38 g p-toluensulfonic acid hydrate was added. The solution was stirred for 1 h and filtered over hyflow. The filtrate was concentrated in vacuo to a volume of 50 mL and stirred for 2 h. The precipitate was filtered and dried. Form A polymorph was obtained as off-white solid (5.4 g).

Figure 10:
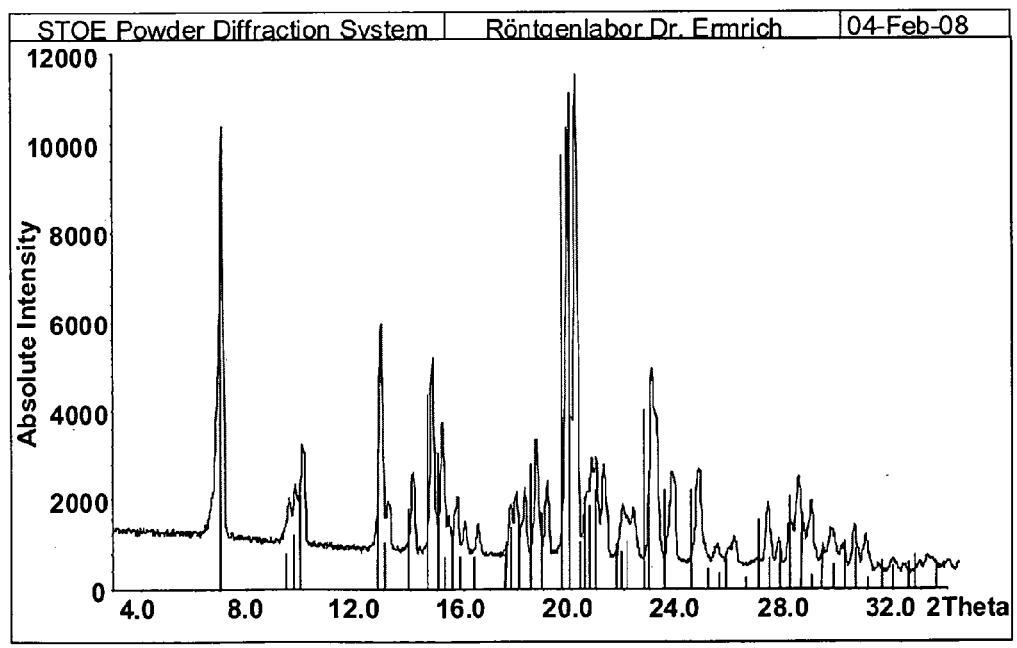
FIG. 10: XRPD pattern of crystalline (E)-N-(2-amino-phenyl)-3-{1-[4-(1-methyl-1H-pyrazol-4-yl)-benzenesulfonyl]-1H-pyrrol-3-yl}-acrylamide toluene-4-sulfonate polymorph A

The characteristic peaks of the X-ray powder diffraction pattern of this salt are substantially summarized in Table 10 and substantially shown in FIG. 10.

TABLE 10

XRPD pattern of crystalline (E)-N-(2-amino-phenyl)-3-{1-[4-(1-methyl-1H-pyrazol-4-yl)-benzenesulfonyl]-1H-pyrrol-3-yl}-acrylamide toluene-4-sulfonate polymorph A comprising the following peaks (relative intensities > 10)

| 2Theta | I(rel) |
|---|---|
| 7.0 | 82.6 |
| 9.7 | 10.8 |
| 9.9 | 18.9 |
| 12.8 | 44.8 |
| 13.9 | 16.2 |
| 14.7 | 39.1 |
| 15.0 | 27.3 |
| 15.5 | 11.6 |
| 17.8 | 12.3 |
| 18.0 | 14.1 |
| 18.5 | 24.9 |
| 18.9 | 15.0 |
| 19.6 | 87.4 |
| 19.9 | 100.0 |
| 20.5 | 18.1 |
| 20.7 | 16.9 |
| 21.0 | 20.0 |
| 22.7 | 36.2 |
| 22.9 | 23.5 |
| 23.5 | 19.9 |
| 24.5 | 19.8 |
| 27.0 | 13.9 |
| 28.1 | 18.7 |
| 28.6 | 14.0 |

Crystalline Polymorph B 100.0 g (E)-N-(2-Amino-phenyl)-3-{1-[4-(1-methyl-1H-pyrazol-4-yl)-benzenesulfonyl]-1H-pyrrol-3-yl}-acrylamide was suspended in 800 mL isopropanol. A solution of 46.8 g p-toluensulfonic acid hydrate in 200 mL isopropanol was added and the suspension was stirred for 22 h. The suspension was filtered and dried to give form B polymorph as off-white solid (139.4 g).

Figure 11:
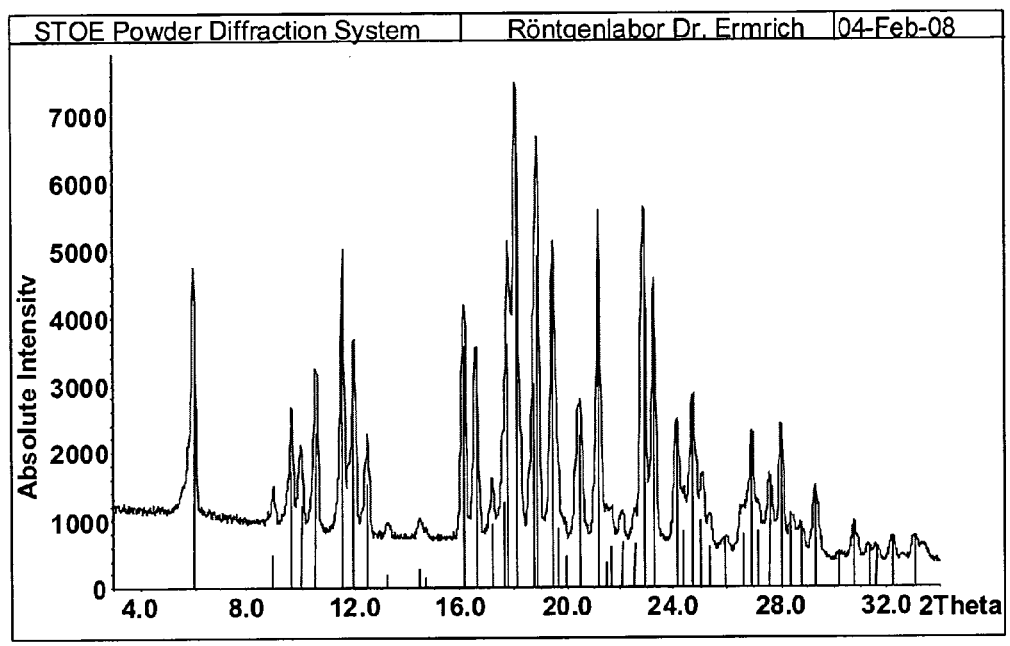
FIG. 11: XRPD pattern of crystalline (E)-N-(2-amino-phenyl)-3-{1-[4-(1-methyl-1H-pyrazol-4-yl)-benzenesulfonyl]-1H-pyrrol-3-yl}-acrylamide toluene-4-sulfonate polymorph B

The characteristic peaks of the X-ray powder diffraction pattern of this salt are substantially summarized in Table 11 and substantially shown in FIG. 11.

TABLE 11

XRPD pattern of crystalline (E)-N-(2-amino-phenyl)-3-{1-[4-(1-methyl-1H-pyrazol-4-yl)-benzenesulfonyl]-1H-pyrrol-3-yl}-acrylamide toluene-4-sulfonate polymorph B comprising the following peaks (relative intensities > 10)

| 2Theta | I(rel) |
|---|---|
| 6.0 | 55.8 |
| 9.6 | 26.0 |
| 10.0 | 18.6 |
| 10.5 | 35.1 |
| 11.6 | 59.9 |
| 12.0 | 43.1 |
| 12.5 | 23.4 |
| 16.1 | 54.5 |
| 16.6 | 45.2 |
| 17.2 | 14.1 |
| 17.6 | 19.3 |
| 17.8 | 55.1 |
| 18.1 | 100.0 |
| 18.7 | 46.3 |
| 18.9 | 75.3 |
| 19.4 | 71.6 |
| 19.7 | 13.3 |
| 20.5 | 34.3 |
| 21.2 | 78.0 |
| 22.1 | 10.1 |
| 22.9 | 85.6 |
| 23.3 | 69.3 |
| 24.1 | 37.7 |
| 24.4 | 12.7 |
| 24.7 | 43.0 |
| 25.0 | 15.0 |
| 25.9 | 11.2 |
| 26.6 | 12.0 |
| 26.9 | 34.6 |
| 27.1 | 12.6 |
| 27.6 | 25.2 |
| 28.0 | 36.8 |
| 28.4 | 16.6 |
| 28.8 | 13.1 |
| 29.3 | 22.5 |
| 30.8 | 15.0 |
| 32.2 | 11.6 |
| 33.0 | 11.7 |

Crystalline Polymorph C 1.0 g Form B polymorph of (E)-N-(2-Amino-phenyl)-3-{1-[4-(1-methyl-1H-pyrazol-4-yl)-benzenesulfonyl]-1H-pyrrol-3-yl}-acrylamide toluene-4-sulfonate was suspended in 10 mL methanol and stirred at 60° C. for 48 h. The suspension was cooled to room temperature, filtered and dried. Form C polymorph was obtained as off-white solid (825 mg).

Figure 12:
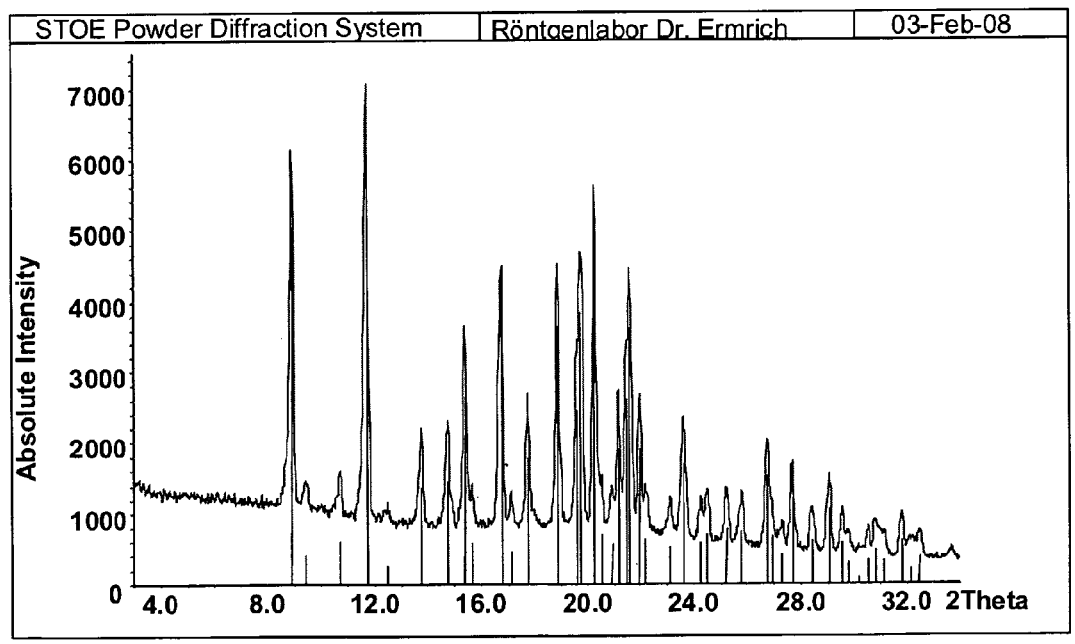
FIG. 12: XRPD pattern of crystalline (E)-N-(2-amino-phenyl)-3-{1-[4-(1-methyl-1H-pyrazol-4-yl)-benzenesulfonyl]-1H-pyrrol-3-yl}-acrylamide toluene-4-sulfonate polymorph C

The characteristic peaks of the X-ray powder diffraction pattern of this salt are substantially summarized in Table 12 and substantially shown in FIG. 12.

TABLE 12

XRPD pattern of crystalline (E)-N-(2-amino-phenyl)-3-{1-[4-(1-methyl-1H-pyrazol-4-yl)-benzenesulfonyl]-1H-pyrrol-3-yl}-acrylamide toluene-4-sulfonate polymorph C comprising the following peaks (relative intensities > 10)

| 2Theta | I(rel) |
|---|---|
| 8.9 | 83.1 |
| 11.7 | 100.0 |
| 13.8 | 22.8 |
| 14.8 | 24.1 |
| 15.4 | 46.3 |
| 16.7 | 60.2 |
| 17.8 | 29.3 |
| 18.9 | 60.2 |
| 19.6 | 40.4 |
| 19.8 | 63.4 |
| 20.3 | 76.9 |
| 20.5 | 11.2 |

TABLE 12-continued

XRPD pattern of crystalline (E)-N-(2-amino-phenyl)-3-{1-[4-(1-methyl-1H-pyrazol-4-yl)-benzenesulfonyl]-1H-pyrrol-3-yl}-acrylamide toluene-4-sulfonate polymorph C comprising the following peaks (relative intensities > 10)

| 2Theta | I(rel) |
|---|---|
| 21.2 | 31.6 |
| 21.5 | 42.9 |
| 21.6 | 59.6 |
| 22.0 | 31.6 |
| 22.2 | 10.2 |
| 23.6 | 27.7 |
| 24.5 | 11.6 |
| 25.2 | 12.9 |
| 25.8 | 12.5 |
| 26.8 | 24.8 |
| 26.9 | 10.9 |
| 27.7 | 20.1 |
| 28.4 | 10.0 |
| 29.1 | 17.6 |

Crystalline Polymorph D 5.0 g (E)-N-(2-Amino-phenyl)-3-{1-[4-(1-methyl-1H-pyrazol-4-yl)-benzenesulfonyl]-1H-pyrrol-3-yl}-acrylamide was suspended in 75 mL MIBK and 2.34 g p-toluensulfonic acid hydrate was added. The suspension was stirred for 4 h, filtered and dried. Form D polymorph was obtained as off-white solid (6.6 g).

Figure 13:
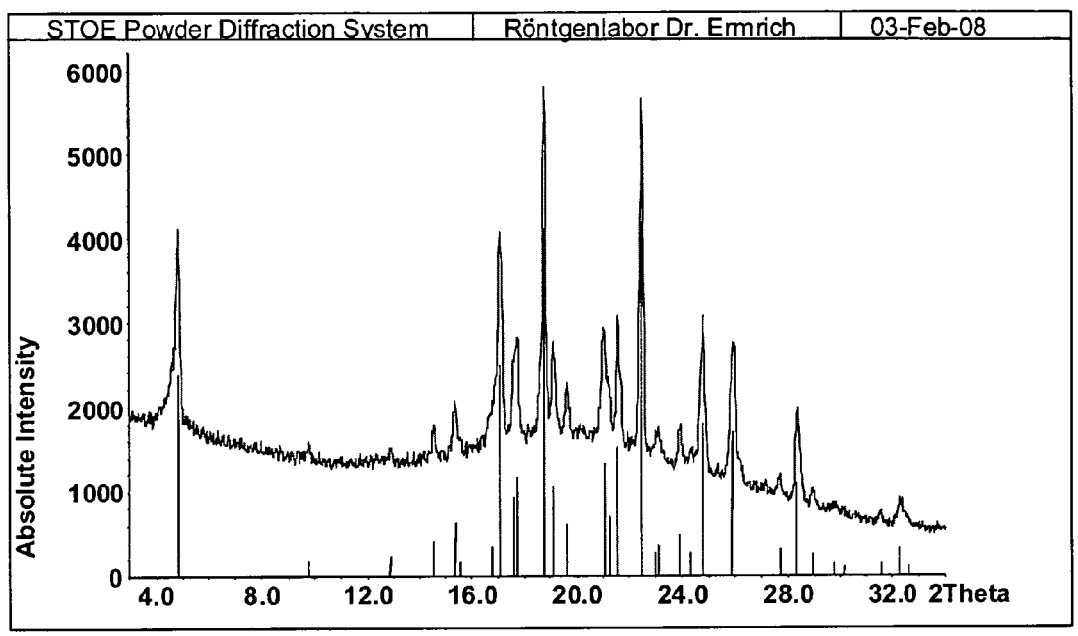
FIG. 13: XRPD pattern of crystalline (E)-N-(2-amino-phenyl)-3-{1-[4-(1-methyl-1H-pyrazol-4-yl)-benzenesulfonyl]-1H-pyrrol-3-yl}-acrylamide toluene-4-sulfonate polymorph D

The characteristic peaks of the X-ray powder diffraction pattern of this salt are substantially summarized in Table 13 and substantially shown in FIG. 13.

TABLE 13

XRPD pattern of crystalline (E)-N-(2-amino-phenyl)-3-{1-[4-(1-methyl-1H-pyrazol-4-yl)-benzenesulfonyl]-1H-pyrrol-3-yl}-acrylamide toluene-4-sulfonate polymorph D comprising the following peaks (relative intensities > 10)

| 2Theta | I(rel) |
|---|---|
| 4.8 | 56.7 |
| 14.5 | 10.0 |
| 15.4 | 14.9 |
| 17.1 | 59.5 |
| 17.6 | 22.0 |
| 17.7 | 27.7 |
| 18.7 | 98.3 |
| 19.1 | 24.9 |
| 19.6 | 14.2 |
| 21.0 | 31.3 |
| 21.2 | 16.6 |
| 21.6 | 36.2 |
| 22.5 | 100.0 |
| 23.9 | 11.4 |
| 24.8 | 43.0 |
| 25.9 | 40.3 |
| 28.4 | 26.1 |

Crystalline Polymorph E 1.0 g Form B polymorph of (E)-N-(2-Amino-phenyl)-3-{1-[(4-(1-methyl-1H-pyrazol-4-yl)-benzenesulfonyl]-1H-pyrrol-3-yl}-acrylamide toluene-4-sulfonate was suspended in 9 mL methanol and 1 mL water and stirred at room temperature for 24 h. The suspension was filtered and dried. Form E polymorph was obtained as off-white solid (826 mg).

Figure 14:
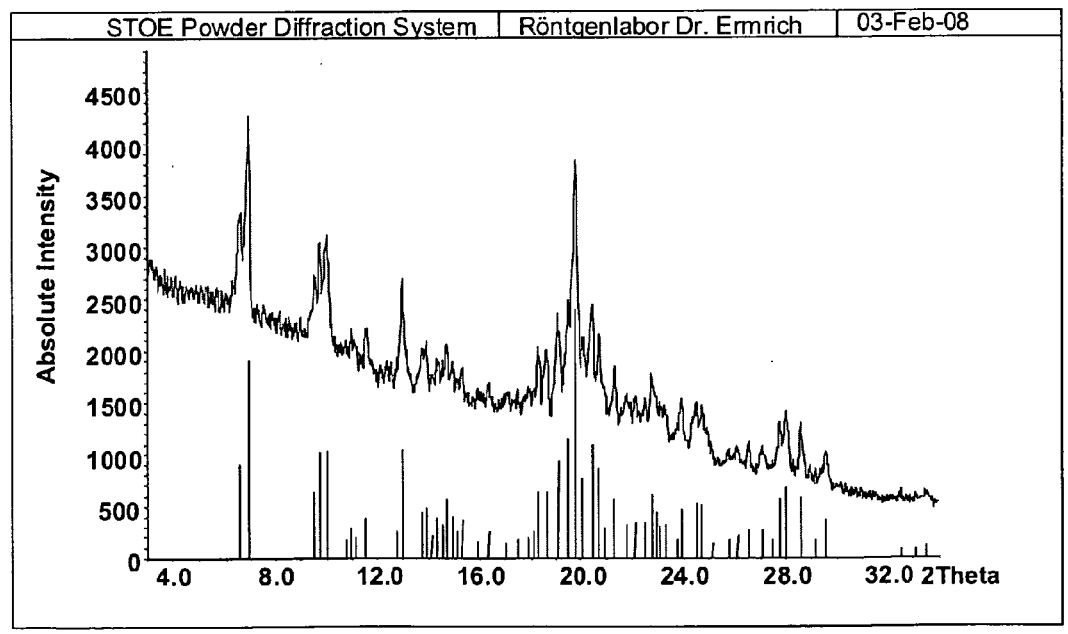
FIG. 14: XRPD pattern of crystalline (E)-N-(2-amino-phenyl)-3-{1-[4-(1-methyl-1H-pyrazol-4-yl)-benzenesulfonyl]-1H-pyrrol-3-yl}acrylamide toluene-4-sulfonate polymorph E

The characteristic peaks of the X-ray powder diffraction pattern of this salt are substantially summarized in Table 14 and substantially shown in FIG. 14.

TABLE 14

XRPD pattern of crystalline (E)-N-(2-amino-phenyl)-3-{1-[4-(1-methyl-1H-pyrazol-4-yl)-benzenesulfonyl]-1H-pyrrol-3-yl}-acrylamide toluene-4-sulfonate polymorph E comprising the following peaks (relative intensities > 10)

| 2Theta | I(rel) |
|---|---|
| 6.6 | 37.7 |
| 6.9 | 79.7 |
| 9.5 | 27.1 |
| 9.7 | 42.5 |
| 10.0 | 43.3 |
| 11.0 | 11.6 |
| 11.6 | 15.7 |
| 12.8 | 10.6 |
| 13.0 | 43.6 |
| 13.7 | 18.0 |
| 13.9 | 20.6 |
| 14.3 | 15.9 |
| 14.6 | 14.0 |
| 14.7 | 23.2 |
| 14.9 | 16.6 |
| 15.1 | 10.1 |
| 15.3 | 15.1 |
| 16.4 | 10.5 |
| 18.2 | 10.1 |
| 18.3 | 26.9 |
| 18.6 | 26.5 |
| 19.1 | 39.3 |
| 19.5 | 47.8 |
| 19.8 | 100.0 |
| 20.1 | 31.8 |
| 20.4 | 45.8 |
| 20.7 | 35.7 |
| 21.0 | 12.1 |
| 21.3 | 23.7 |
| 21.8 | 13.9 |
| 22.1 | 14.1 |
| 22.5 | 14.5 |
| 22.8 | 25.5 |
| 22.9 | 17.9 |
| 23.1 | 12.3 |
| 23.3 | 13.5 |
| 23.9 | 19.6 |
| 24.5 | 21.5 |
| 24.7 | 21.1 |
| 26.5 | 11.5 |
| 27.1 | 11.1 |
| 27.8 | 23.3 |
| 28.0 | 28.1 |
| 28.6 | 24.1 |
| 29.6 | 15.2 |

Crystalline Polymorph F 200 mg Form A polymorph of (E)-N-(2-Amino-phenyl)-3-{1-[4-(1-methyl-1H-pyrazol-4-yl)-benzenesulfonyl]-1H-pyrrol-3-yl}-acrylamide toluene-4-sulfonate was suspended in 1.8 mL ethylmethylketone and 0.2 mL water and was stirred for 18 h. The suspension was filtered and dried. Form F polymorph was obtained as off-white solid (101 mg).

Figure 15:
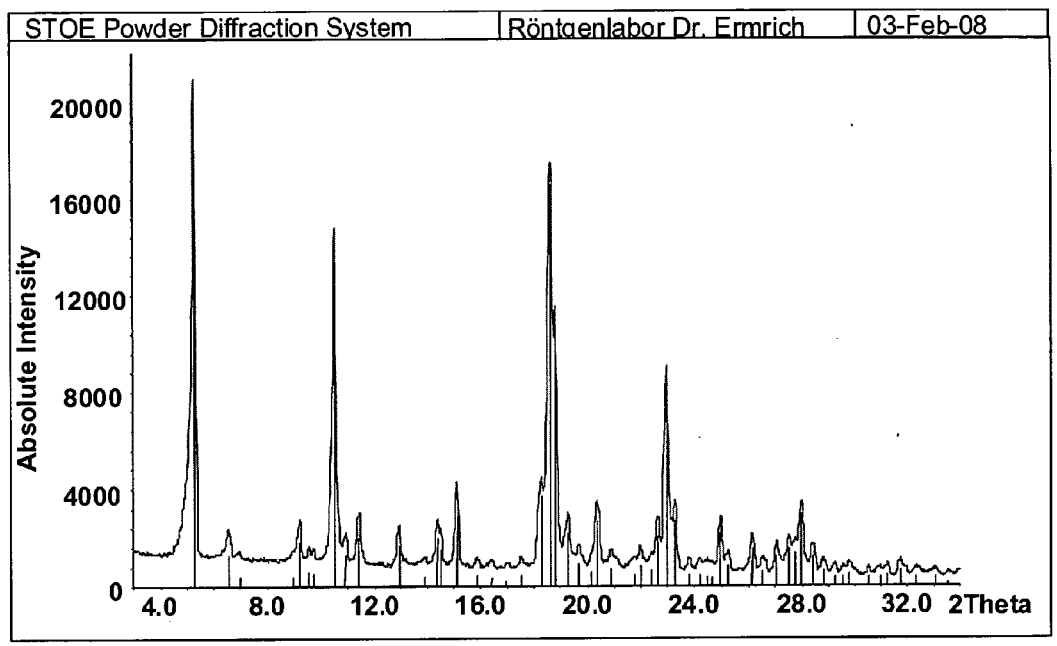
FIG. 15: XRPD pattern of crystalline (E)-N-(2-amino-phenyl)-3-{1-[4-(1-methyl-1-pyrazol-4-yl)-benzenesulfonyl]-1H-pyrrol-3-yl}-acrylamide toluene-4-sulfonate polymorph F

The characteristic peaks of the X-ray powder diffraction pattern of this salt are substantially summarized in Table 15 and substantially shown in FIG. 15.

TABLE 15

XRPD pattern of crystalline (E)-N-(2-amino-phenyl)-3-{1-[4-(1-methyl-1H-pyrazol-4-yl)-benzenesulfonyl]-1H-pyrrol-3-yl}-acrylamide toluene-4-sulfonate polymorph F comprising the following peaks (relative intensities > 10)

| 2Theta | I(rel) |
|---|---|
| 5.3 | 100.0 |
| 10.5 | 70.0 |
| 11.4 | 10.3 |

TABLE 15-continued

XRPD pattern of crystalline (E)-N-(2-amino-phenyl)-3-{1-[4-(1-methyl-1H-pyrazol-4-yl)-benzenesulfonyl]-1H-pyrrol-3-yl}-acrylamide toluene-4-sulfonate polymorph F comprising the following peaks (relative intensities > 10)

| 2Theta | I(rel) |
|---|---|
| 15.1 | 18.4 |
| 18.3 | 19.0 |
| 18.6 | 85.6 |
| 18.8 | 55.5 |
| 19.3 | 11.1 |
| 20.4 | 14.0 |
| 22.6 | 10.6 |
| 22.9 | 42.9 |
| 23.3 | 13.7 |
| 25.0 | 11.2 |
| 28.0 | 15.3 |

Crystalline Polymorph G 1.00 g Form C polymorph of (E)-N-(2-Amino-phenyl)-3-{1-[4-(1-methyl-1H-pyrazol-4-yl)-benzenesulfonyl]-1H-pyrrol-3-yl}-acrylamide toluene-4-sulfonate was suspended in 9 mL acetone and 1 mL water and was stirred for 24 h. The suspension was filtered and dried. Form G polymorph was obtained as off-white solid (867 mg).

Figure 16:
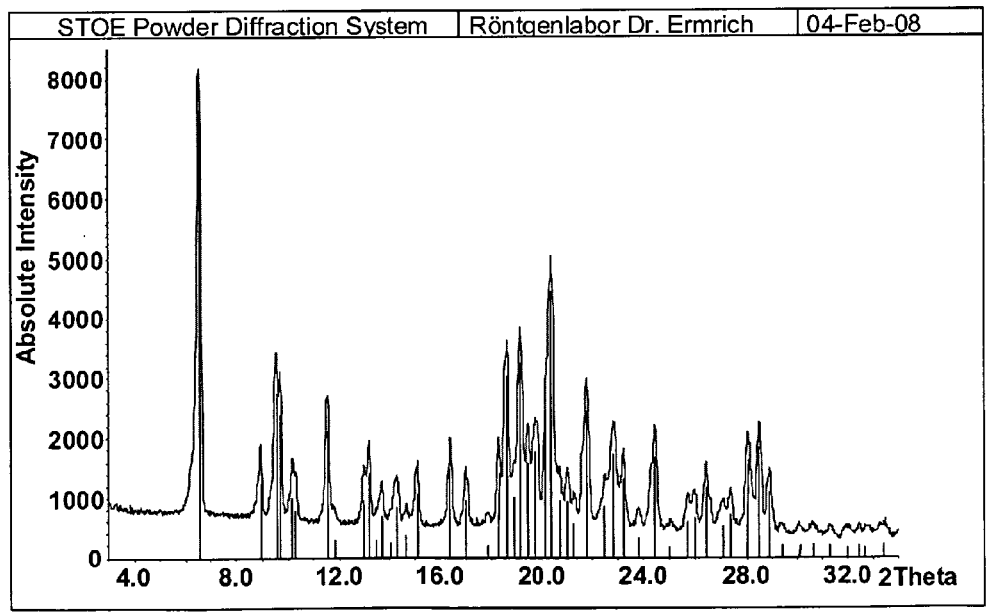
FIG. 16: XRPD pattern of crystalline (E)-N-(2-amino-phenyl)-3-{1-[4-(1-methyl-1H-pyrazol-4-yl)-benzenesulfonyl]-1H-pyrrol-3-yl}-acrylamide toluene-4-sulfonate polymorph G

The characteristic peaks of the X-ray powder diffraction pattern of this salt are substantially summarized in Table 16 and substantially shown in FIG. 16.

TABLE 16

XRPD pattern of crystalline (E)-N-(2-amino-phenyl)-3-{1-[4-(1-methyl-1H-pyrazol-4-yl)-benzenesulfonyl]-1H-pyrrol-3-yl}-acrylamide toluene-4-sulfonate polymorph G comprising the following peaks (relative intensities > 10)

| 2Theta | I(rel) |
|---|---|
| 6.6 | 100.0 |
| 8.9 | 16.0 |
| 9.5 | 36.6 |
| 9.7 | 31.7 |
| 10.2 | 13.2 |
| 10.3 | 10.3 |
| 11.5 | 27.9 |
| 13.0 | 12.6 |
| 13.2 | 18.5 |
| 14.3 | 11.2 |
| 15.1 | 13.8 |
| 16.4 | 19.3 |
| 17.0 | 12.6 |
| 18.3 | 18.6 |
| 18.6 | 40.1 |
| 18.9 | 13.2 |
| 19.2 | 43.2 |
| 19.4 | 21.0 |
| 19.8 | 23.4 |
| 20.2 | 32.4 |
| 20.4 | 59.3 |
| 20.7 | 12.4 |
| 21.0 | 12.1 |
| 21.7 | 32.2 |
| 22.5 | 11.6 |
| 22.8 | 22.8 |
| 23.2 | 17.3 |
| 24.4 | 22.3 |
| 26.4 | 15.3 |
| 28.1 | 21.8 |
| 28.5 | 24.5 |
| 28.9 | 14.5 |

Crystalline Polymorph H 7.0 g of (E)-N-(2-Amino-phenyl)-3-{1-[4-(1-methyl-1H-pyrazol-4-yl)-benzenesulfonyl]-1H-pyrrol-3-yl}-acrylamide (15.6 mmol) was suspended in 126 ml of a 5:1 mixture of acetone and water. The suspension was heated to reflux until all material was solved. The hot solution was filtered through a glass fiber filter and the filter was washed with 4 ml of the hot solvent mixture. The filtrates were combined. 107 ml of the solvent was distilled of in vacuum, while the free base crystallized again. The precipitate was filtered of and used without drying.

12.0 g of (E)-N-(2-Amino-phenyl)-3-{1-[4-(1-methyl-1H-pyrazol-4-yl)-benzenesulfonyl]-1H-pyrrol-3-yl}-acrylamide (free base, 15.6 mmol) with a water content of 42% was suspended in a mixture of 53 ml 2-propanole and 107 ml water at room temperature. 3.6 g of p-toluene sulfonic acid monohydrate (18.8 mmol) was dissolved in 32 ml of 2-propanole and 8 ml of water. The solution was added dropwise to the suspension of the free base over a period of 1 hour. The suspension was stirred for further 3 days at room temperature. The precipitate was filtered off, washed with 5 ml of the solvent mixture used for the crystallization, and dried in vacuum at 40° C. for 18 hours. Yield: 9.43 g; water content by Karl Fischer Titration: 2.7%.

Figure 17:
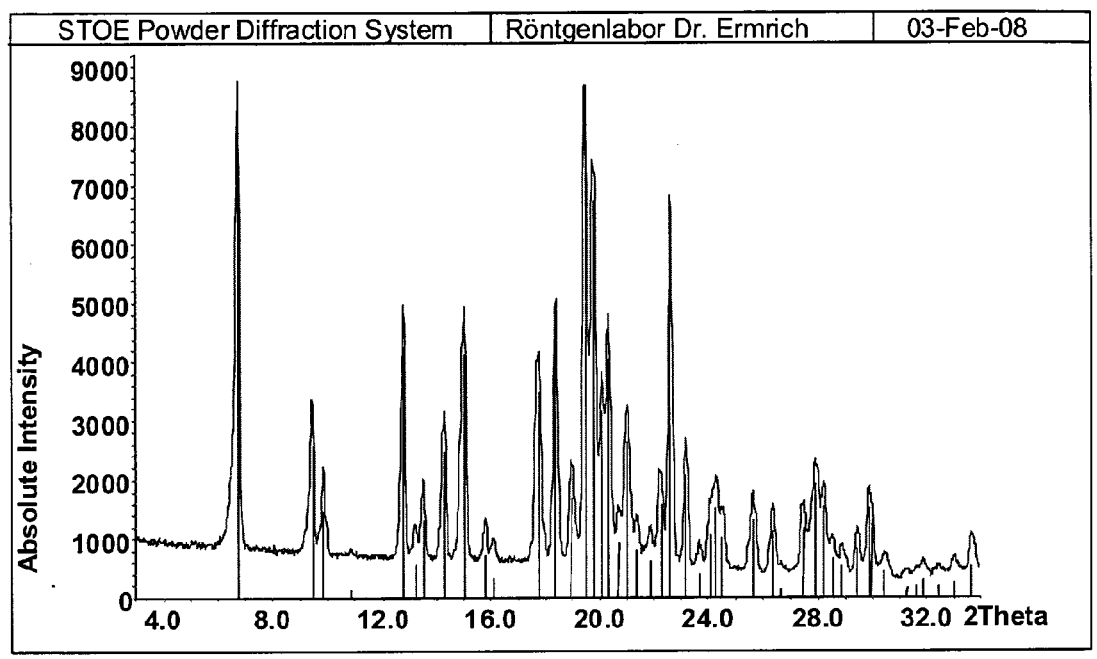
FIG. 17: XRPD pattern of crystalline (E)-N-(2-amino-phenyl)-3-{1-[4-(1-methyl-1H-pyrazol-4-yl)-benzenesulfonyl]-1H-pyrrol-3-yl}-acrylamide toluene-4-sulfonate polymorph H

The characteristic peaks of the X-ray powder diffraction pattern of this salt are substantially summarized in Table 17 and substantially shown in FIG. 17.

TABLE 17

XRPD pattern of crystalline (E)-N-(2-amino-phenyl)-3-{1-[4-(1-methyl-1H-pyrazol-4-yl)-benzenesulfonyl]-1H-pyrrol-3-yl}-acrylamide toluene-4-sulfonate polymorph H comprising the following peaks (relative intensities > 10)

| 2Theta | I(rel) |
|---|---|
| 6.7 | 96.9 |
| 9.4 | 32.1 |
| 9.9 | 18.2 |
| 12.8 | 52.8 |
| 13.5 | 16.3 |
| 14.3 | 30.7 |
| 15.0 | 51.1 |
| 17.7 | 43.4 |
| 18.4 | 54.6 |
| 19.0 | 20.8 |
| 19.5 | 100.0 |
| 19.8 | 83.3 |
| 20.1 | 39.4 |
| 20.3 | 50.3 |
| 20.7 | 11.6 |
| 21.0 | 32.5 |
| 22.2 | 19.3 |
| 22.6 | 76.8 |
| 23.2 | 25.9 |
| 24.1 | 3.2 |
| 24.3 | 18.7 |
| 24.5 | 12.3 |
| 25.7 | 16.2 |
| 26.4 | 13.8 |
| 27.5 | 14.4 |
| 27.9 | 23.8 |
| 28.2 | 19.1 |
| 29.5 | 10.0 |
| 29.9 | 19.0 |
| 30.0 | 16.0 |

(E)-N-(2-Amino-phenyl)-3-{1-[4-(1-methyl-1H-pyrazol-4-yl)-benzenesulfonyl]-1H-pyrrol-3-yl}-acrylamide naphthalene-2-sulfonate Crystalline Polymorph A+B 2.00 g (E)-N-(2-Amino-phenyl)-3-{1-[4-(1-methyl-1H-pyrazol-4-yl)-benzene sulfonyl]-1H-pyrrol-3-yl}-acrylamide was suspended in 40 mL isopropanol. 1.46 g naphthalene-2-sulfonic acid (70%) was added and the suspension was stirred for 24 h. The suspension was filtered, the filter cake was washed with 20 mL isopropanol and dried. An off-white solid (2.72 g) was obtained.

Figure 18:
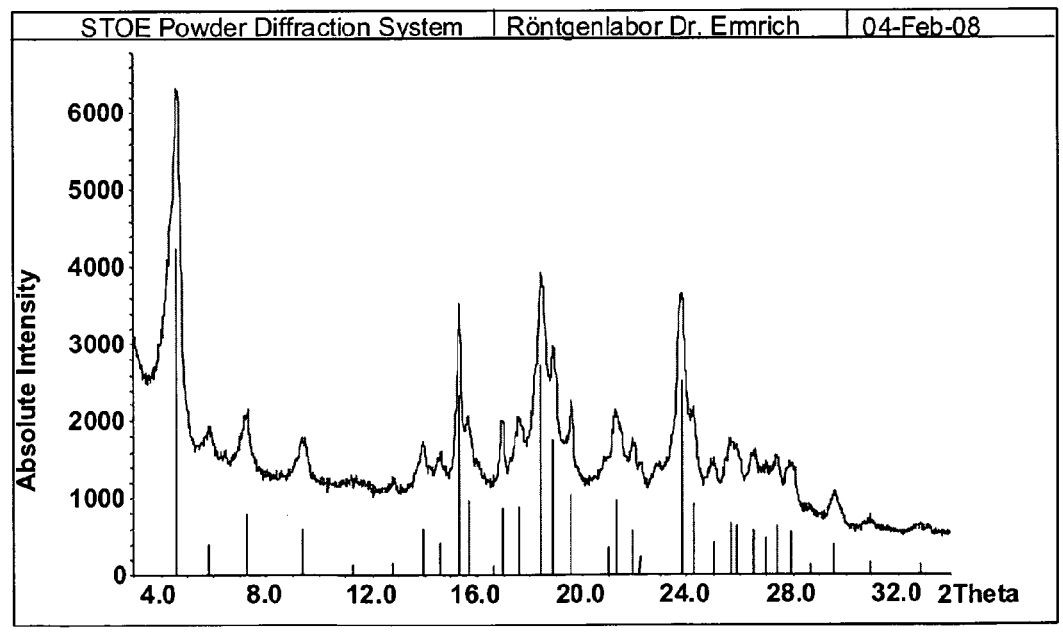
FIG. 18: XRPD pattern of crystalline (E)-N-(2-amino-phenyl)-3-{1-[4-(1-methyl-1H-pyrazol-4-yl)-benzenesulfonyl]-1H-pyrrol-3-yl}-acrylamide naphthalene-2-sulfonate polymorph A+B

The characteristic peaks of the X-ray powder diffraction pattern of this salt are substantially summarized in Table 18 and substantially shown in FIG. 18.

TABLE 18

XRPD pattern of crystalline (E)-N-(2-amino-phenyl)-3-{1-[4-(1-methyl-1H-pyrazol-4-yl)-benzenesulfonyl]-1H-pyrrol-3-yl}-acrylamide naphthalene-2-sulfonate polymorph A + B comprising the following peaks (relative intensities > 10)

| 2Theta | I(rel) |
|---|---|
| 4.6 | 100.0 |
| 7.3 | 18.2 |
| 9.4 | 14.0 |
| 13.9 | 14.1 |
| 14.6 | 10.0 |
| 15.3 | 54.6 |
| 15.7 | 22.3 |
| 17.0 | 20.2 |
| 17.6 | 20.9 |
| 18.5 | 64.0 |
| 18.9 | 41.4 |
| 19.6 | 24.4 |
| 21.3 | 22.4 |
| 21.9 | 13.4 |
| 23.8 | 59.2 |
| 24.2 | 21.5 |
| 25.7 | 16.1 |
| 25.9 | 14.7 |
| 26.5 | 13.7 |
| 27.0 | 11.3 |
| 27.4 | 15.0 |
| 27.9 | 12.8 |

Crystalline Polymorph A+B 2.00 g (E)-N-(2-Amino-phenyl)-3-{1-[4-(1-methyl-1H-pyrazol-4-yl)-benzene sulfonyl]-1H-pyrrol-3-yl}-acrylamide was suspended in 40 mL isopropanol. 1.46 g naphthalene-2-sulfonic acid (70%) was added and the suspension was stirred for 21 h. The suspension was filtered and dried. An off-white solid (2.82 g) was obtained.

Figure 19:
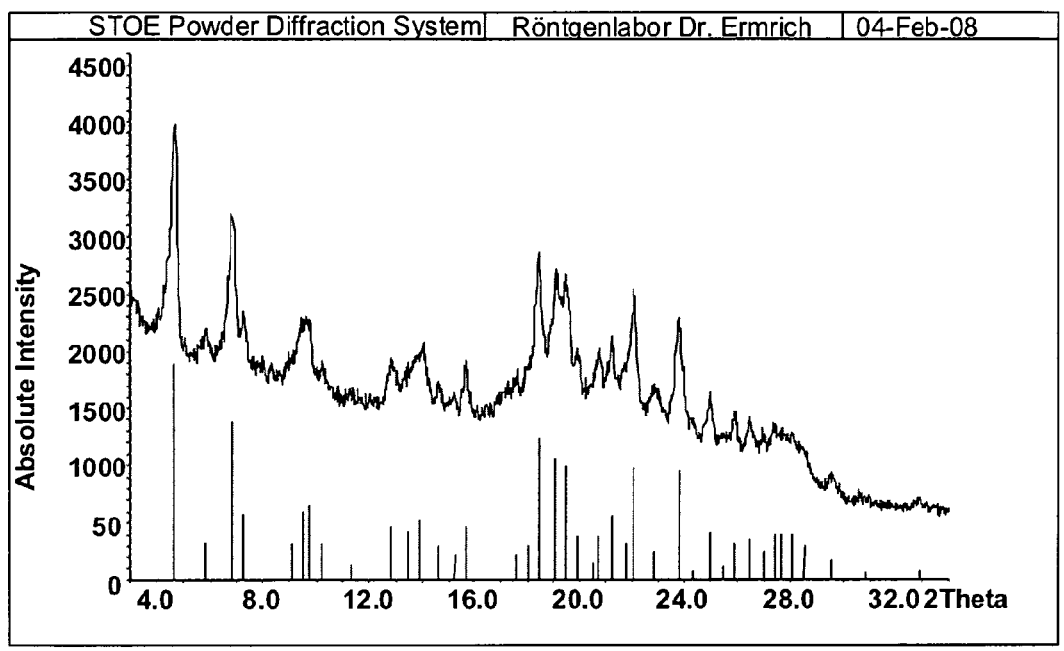
FIG. 19: XRPD pattern of crystalline (E)-N-(2-amino-phenyl)-3-{1-[4-(1-methyl-1H-pyrazol-4-yl)-benzenesulfonyl]-1H-pyrrol-3-yl}-acrylamide naphthalene-2-sulfonate polymorph A+B

The characteristic peaks of the X-ray powder diffraction pattern of this salt are substantially summarized in Table 19 and substantially shown in FIG. 19.

TABLE 19

XRPD pattern of crystalline (E)-N-(2-amino-phenyl)-3-{1-[4-(1-methyl-1H-pyrazol-4-yl)-benzenesulfonyl]-1H-pyrrol-3-yl}-acrylamide naphthalene-2-sulfonate polymorph A + B comprising the following peaks (relative intensities > 10)

| 2Theta | I(rel) |
|---|---|
| 4.7 | 100.0 |
| 5.8 | 17.2 |
| 6.8 | 73.1 |
| 7.3 | 30.1 |
| 9.1 | 16.6 |
| 9.5 | 31.4 |
| 9.7 | 34.0 |
| 10.2 | 16.7 |
| 12.8 | 24.7 |
| 13.5 | 22.2 |
| 13.9 | 27.3 |
| 14.6 | 15.9 |
| 15.2 | 11.3 |
| 15.6 | 24.2 |
| 17.6 | 11.2 |
| 18.0 | 15.6 |
| 18.5 | 65.2 |

TABLE 19-continued

XRPD pattern of crystalline (E)-N-(2-amino-phenyl)-3-{1-[4-(1-methyl-1H-pyrazol-4-yl)-benzenesulfonyl]-1H-pyrrol-3-yl}-acrylamide naphthalene-2-sulfonate polymorph A + B comprising the following peaks (relative intensities > 10)

| 2Theta | I(rel) |
|---|---|
| 19.1 | 55.8 |
| 19.5 | 52.5 |
| 19.9 | 20.2 |
| 20.8 | 19.8 |
| 21.2 | 29.6 |
| 21.8 | 16.9 |
| 22.1 | 51.4 |
| 22.8 | 12.9 |
| 23.8 | 49.9 |
| 25.0 | 21.2 |
| 25.9 | 16.3 |
| 26.4 | 18.3 |
| 27.0 | 12.7 |
| 27.4 | 20.5 |
| 27.7 | 20.9 |
| 28.1 | 20.4 |
| 28.5 | 15.7 |

Crystalline Polymorph C 1.00 g (E)-N-(2-Amino-phenyl)-3-{1-[4-(1-methyl-1H-pyrazol-4-yl)-benzene sulfonyl]-1H-pyrrol-3-yl}-acrylamide was suspended in 15 mL methanol. 1.46 g naphthalene-2-sulfonic acid (70%) was added and the solution was filtered. Seeding crystals were added to the filtrate and the suspension was stirred for 1 h. The suspension was filtered and dried. An off-white solid (1.28 g) was obtained.

Figure 20:
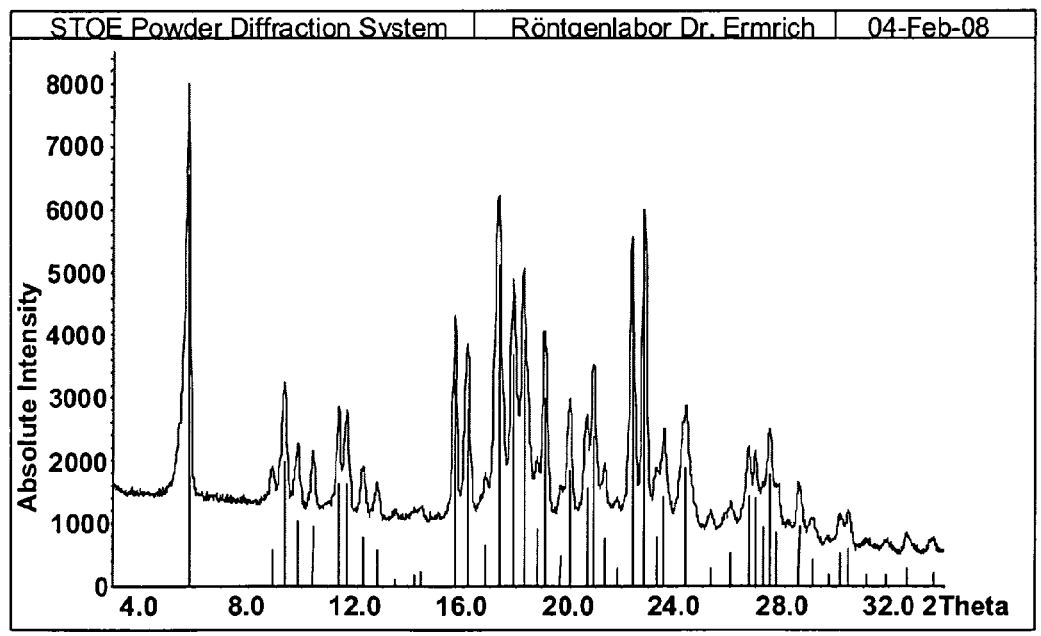
FIG. 20: XRPD pattern of crystalline (E)-N-(2-amino-phenyl)-3-{1-[4-(1-methyl-1H-pyrazol-4-yl)-benzenesulfonyl]-1H-pyrrol-3-yl}-acrylamide naphthalene-2-sulfonate polymorph C

The characteristic peaks of the X-ray powder diffraction pattern of this salt are substantially summarized in Table 20 and substantially shown in FIG. 20.

TABLE 20

XRPD pattern of crystalline (E)-N-(2-amino-phenyl)-3-{1-[4-(1-methyl-1H-pyrazol-4-yl)-benzenesulfonyl]-1H-pyrrol-3-yl}-acrylamide naphthalene-2-sulfonate polymorph C comprising the following peaks (relative intensities > 10)

| 2Theta | I(rel) |
|---|---|
| 5.8 | 100.0 |
| 9.4 | 30.2 |
| 9.9 | 15.5 |
| 10.4 | 14.4 |
| 11.4 | 25.2 |
| 11.7 | 25.2 |
| 12.3 | 12.0 |
| 15.7 | 50.2 |
| 16.2 | 42.9 |
| 17.3 | 78.4 |
| 17.9 | 56.6 |
| 18.3 | 59.9 |
| 18.8 | 13.7 |
| 19.1 | 45.6 |
| 20.0 | 27.8 |
| 20.7 | 23.6 |
| 20.9 | 36.3 |
| 21.3 | 11.5 |
| 22.4 | 67.3 |
| 22.9 | 75.3 |
| 23.3 | 11.7 |
| 23.6 | 21.7 |
| 24.4 | 28.7 |
| 26.7 | 21.7 |
| 27.0 | 21.5 |
| 27.3 | 14.0 |
| 27.5 | 27.2 |
| 27.8 | 13.0 |
| 28.6 | 14.3 |

Commercial Utility

The (E)-N-(2-amino-phenyl)-3-{1-[4-(1-methyl-1H-pyrazol-4-yl)-benzenesulfonyl]-1H-pyrrol-3-yl}-acrylamide salts according to this invention have valuable pharmacological properties and effects, which make them commercially applicable, such as e.g. they are commercially utilizable by properties related with inhibiting histone deacetylase activity and function.

"Histone deacetylase" (HDAC) means an enzyme with an activity towards the ε-acetyl group of lysine residues within a substrate protein. HDAC substrates are histone H2A, H2B, H3 or H4 proteins and isoforms but substrate proteins different to histones like, but not limited to, heat shock protein 90 (Hsp90), tubulin or the tumor suppressor protein p53 exist. In particular histone deacetylases catalyse the hydrolysis the ε-acetyl group of lysine residues within these substrate proteins, forming the free amino group of lysine.

Inhibition of histone deacetylase by the (E)-N-(2-amino-phenyl)-3-{1-[4-(1-methyl-1H-pyrazol-4-yl)-benzenesulfonyl]-1H-pyrrol-3-yl}-acrylamide salts according to this invention means inhibiting the activity and function of one or more HDAC isoenzymes, in particular isoenzymes selected from the so far known histone deacetylases, namely HDAC 1, 2, 3 and 8 (class I) and HDAC 4, 5, 6, 7, 9 and 10 (class II), HDAC 11 as well as the NAD+ dependent class III (Sir2 homologues). In some preferred embodiments this inhibition is at least about 50%, more preferable at least 75% and still more preferable above 90%. Preferably, this inhibition is specific to a specific histone deacetylase class (e.g. HDAC class I enzymes), a selection of isoenzymes of highest pathophysiological relevance (e.g. HDAC 1, 2, 3 enzymes) or a single isoenzyme (e.g. the HDAC 1 enzyme). A histone deacetylase inhibitor in the meaning of this invention is therefore a compound capable of interacting with a histone deacetylase and inhibiting its activity, in particular its enzymatic activity. In this context "head group" defines the residues within a histone deacetylase inhibitor responsible for interacting with the active site of the enzyme, e.g. the $Zn^{2+}$ ion.

The inhibition of histone deacetylases is determined in biochemical assays of various formats and sources of enzymatic activity. HDAC activity is used either derived from nuclear or cellular extracts or by heterologous expression of defined HDAC isoenzymes in E. coli, insect cells or mammalian cells. Since HDAC isoenzymes are active in multiprotein complexes and form homo- and heterodimers, nuclear extracts derived from human cancer cells, for example the human cervical carcinoma cell line HeLa, are preferred. These nuclear extracts contain class I and class II enzymes, but are enriched in class I enzymes. For expression of recombinant HDAC isoenzymes, mammalian expression systems like HEK293 cells are preferred. The HDAC isoenzyme is expressed as a fusion protein with an affinity tag, like the FLAG epitope. By affinity chromatography, the tagged protein is purified alone or in complex with endogenous proteins (e.g. other HDAC isoenzymes and coactivators/platform proteins). The biochemical assays are well described and well known to persons skilled in the art. As substrates, histone proteins, peptides derived from histone proteins or other HDAC substrates as well as acetylated lysine mimetics are used. One preferred promiscuous HDAC substrate is the tripeptide Ac-NH-GGK(Ac), coupled with the fluorophore 7-aminomethylcoumarin (AMC).

The invention further relates to the use of the (E)-N-(2-amino-phenyl)-3-{1-[4-(1-methyl-1H-pyrazol-4-yl)-benzenesulfonyl]-1H-pyrrol-3-yl}-acrylamide salts according to this invention for inhibiting histone deacetylase activity in cells and tissues, causing hyperacetylation of substrate proteins and as functional consequence, for example, the induction or repression of gene expression, induction of protein degradation, cell cycle arrest, induction of differentiation and/or induction of apoptosis.

The cellular activity of a histone deacetylase inhibitor includes any cellular effect related to histone deacetylase inhibition, in particular protein hyperacetylation, transcriptional repression and activation, induction of apoptosis, differentiation and/or cytotoxicity.

The term "induction of apoptosis" and analogous terms are used to identify a compound which executes programmed cell death in cells contacted with that compound. "Apoptosis" is defined by complex biochemical events within the contacted cell, such as the activation of cysteine specific proteinases ("caspases") and the fragmentation of chromatin. Induction of apoptosis in cells contacted with the compound might not necessarily be coupled with inhibition of cell proliferation or cell differentiation. Preferably, the inhibition of proliferation, induction of differentiation and/or induction of apoptosis is specific to cells with aberrant cell growth.

"Cytotoxicity" in general means arresting proliferation and/or inducing apoptotic cell death in vitro in mammalian cells, in particular human cancer cells.

"Induction of differentiation" is defined as a process of cellular reprogramming leading to a reversible or irreversible cell cycle arrest in G0 and re-expression of a subset of genes typical for a certain specialized normal cell type or tissue (e.g. re-expression of milk fat proteins and fat in mammary carcinoma cells).

"Cytotoxicity" in general means arresting proliferation and/or inducing apoptotic cell death in vitro in mammalian cells, in particular human cancer cells.

Assays for quantification of cell proliferation, apoptosis or differentiation are well known to experts and state of the art. For example, metabolic activity which is linked to cellular proliferation is quantified using the Alamar Blue/Resazurin assay (O'Brian et al. Eur j Biochem 267, 5421-5426, 2000) and induction of apoptosis is quantified by measurement of chromatin fragmentation with the cell death detection ELISA commercialized by Roche. Examples for cellular assays for the determination of hyperacetylation of HDAC substrates are given by measuring core histone acetylation using specific antibodies by Western blotting, reporter gene assays using respective responsive promoters or promoter elements (e.g. the p21 promotor or the sp1 site as responsive element) or finally by image analysis again using acetylation specific antibodies for core histone proteins.

The (E)-N-(2-amino-phenyl)-3-{1-[4-(1-methyl-1H-pyrazol-4-yl)-benzenesulfonyl]-1H-pyrrol-3-yl}-acrylamide salts according to this invention can be commercially applicable due to their HDAC inhibitory, anti-proliferative and/or apoptosis inducing activity, which may be beneficial in the therapy or prophylaxis of diseases responsive thereto, such as e.g. any of those diseases mentioned herein.

The invention further relates to a method for inhibiting, treating, ameliorating or preventing cellular neoplasia by administration of an effective amount of a (E)-N-(2-amino-phenyl)-3-{1-[4-(1-methyl-1H-pyrazol-4-yl)-benzenesulfonyl]-1H-pyrrol-3-yl}-acrylamide salt according to this invention to a mammal, in particular a human in need of such treatment. A "neoplasia" is defined by cells displaying aberrant cell proliferation and/or survival and/or a block in differentiation. The term "neoplasia" includes benign neoplasia, which is described by hyperproliferation of cells, incapable of forming an aggressive, metastasizing tumor in vivo, and, in contrast, malignant neoplasia, which is described by cells with multiple cellular and biochemical abnormalities, capable of forming a systemic disease, for example forming tumor metastasis in distant organs.

The (E)-N-(2-amino-phenyl)-3-{1-[4-(1-methyl-1H-pyrazol-4-yl)-benzenesulfonyl]-1H-pyrrol-3-yl}-acrylamide salts according to this invention can be particularly used for the treatment of malignant neoplasia, also described as cancer, characterized by tumor cells finally metastasizing into distinct organs or tissues. Examples of malignant neoplasia treated with the (E)-N-(2-amino-phenyl)-3-{1-[4-(1-methyl-1H-pyrazol-4-yl)-benzenesulfonyl]-1H-pyrrol-3-yl}-acrylamide salts according to the present invention include solid and hematological tumors. Solid tumors are exemplified by tumors of the breast, bladder, bone, brain, central and peripheral nervous system, colon, endocrine glands (e.g. thyroid and adrenal cortex), esophagus, endometrium, germ cells, head and neck, kidney, liver, lung, larynx and hypopharynx, mesothelioma, ovary, pancreas, prostate, rectum, renal, small intestine, soft tissue, testis, stomach, skin, ureter, vagina and vulva. Malignant neoplasia include inherited cancers exemplified by Retinoblastoma and Wilms tumor. In addition, malignant neoplasia include primary tumors in said organs and corresponding secondary tumors in distant organs ("tumor metastases"). Hematological tumors are exemplified by aggressive and indolent forms of leukemia and lymphoma, namely non-Hodgkins disease, chronic and acute myeloid leukemia (CML/AML), acute lymphoblastic leukemia (ALL), Hodgkins disease, multiple myeloma and T-cell lymphoma. Also included are myelodysplastic syndrome, plasma cell neoplasia, paraneoplastic syndromes, cancers of unknown primary site as well as AIDS related malignancies.

It is to be noted that a cancer disease as well as a malignant neoplasia does not necessarily require the formation of metastases in distant organs. Certain tumors exert devastating effects on the primary organ itself through their aggressive growth properties. These can lead to the destruction of the tissue and organ structure finally resulting in failure of the assigned organ function.

Neoplastic cell proliferation might also effect normal cell behaviour and organ function. For example the formation of new blood vessels, a process described as neovascularization, is induced by tumors or tumor metastases. The (E)-N-(2-amino-phenyl)-3-{1-[4-(1-methyl-1H-pyrazol-4-yl)-benzenesulfonyl]-1H-pyrrol-3-yl}-acrylamide salts according to this invention can be commercially applicable for treatment of pathophysiological relevant processes caused by benign or neoplastic cell proliferation, such as but not limited to neovascularization by unphysiological proliferation of vascular endothelial cells.

Drug resistance is of particular importance for the frequent failure of standard cancer therapeutics. This drug resistance is caused by various cellular and molecular mechanisms like overexpression of drug efflux pumps, mutation within the cellular target protein or fusion proteins formed by chromosomal translocations. The commercial applicability of the (E)-N-(2-amino-phenyl)-3-{1-[4-(1-methyl-1H-pyrazol-4-yl)benzenesulfonyl]-1H-pyrrol-3-yl}acrylamide salts according to the present invention is not limited to $1^{st}$ line treatment of patients. Patients with resistance to cancer chemotherapeutics or target specific anti-cancer drugs can be also amenable for treatment with these (E)-N-(2-amino-phenyl)-3-{1-[4-(1-methyl-1H-pyrazol-4-yl)-benzenesulfonyl]-1H-pyrrol-3-yl}-acrylamide salts for e.g. $2^{nd}$ or $3^{rd}$ line treatment cycles. A prominent example is given by acute promyelocytic leukemia patients with the PML-RARα fusion protein, resistant to standard therapy with retinoids. These patients can be resensitized towards retinoids by treatment with HDAC inhibitory drugs like the (E)-N-(2-amino-phenyl)-3-{1-[4-(1-methyl-1H-pyrazol-4-yl)-benzenesulfonyl]-1H-pyrrol-3-yl}-acrylamide salts according to the present invention.

The invention further provides to a method for treating a mammal, in particular a human, bearing a disease different to cellular neoplasia, sensitive to histone deacetylase inhibitor therapy comprising administering to said mammal a pharmacologically active and therapeutically effective and tolerable amount of a (E)-N-(2-amino-phenyl)-3-{1-[4-(1-methyl-1H-pyrazol-4-yl)-benzenesulfonyl]-1H-pyrrol-3-yl}-acrylamide salt according to this invention. These non malignant diseases include (i) arthropathies and osteopathological diseases such as rheumatoid arthritis, osteoarthritis, gout, polyarthritis and psoriatic arthritis,
(ii) autoimmune diseases like systemic lupus erythematosus and transplant rejection,
(iii) hyperproliferative diseases such as psoriasis or smooth muscle cell proliferation including vascular proliferative disorders, atherosclerosis and restenosis,
(iv) acute and chronic inflammatory diseases and dermal diseases such as ulcerative colitis, Crohn's disease, allergic rhinitis, allergic dermatitis, cystic fibrosis, chronic obstructive bronchitis and asthma,
(v) endometriosis, uterine fibroids, endometrial hyperplasia and benign prostate hyperplasia,
(vi) cardiac dysfunction,
(vii) inhibiting immunosuppressive conditions like HIV infections,
(viii) neuropathological disorders like Parkinson's disease, Alzheimer disease or polyglutamine related disorders, and
(ix) pathological conditions amenable to treatment by potentiating of endogenous gene expression as well as enhancing transgene expression in gene therapy.

The (E)-N-(2-amino-phenyl)-3-{1-[4-(1-methyl-1H-pyrazol-4-yl)-benzenesulfonyl]-1H-pyrrol-3-yl}-acrylamide salts according to the present invention may be commercially applicable for treatment, prevention or amelioration of the diseases of benign and malignant behavior as described herein, such as, for example, (hyper)proliferative diseases and/or disorders responsive to induction of apoptosis and/or disorders responsive to cell differentiation, e.g. benign or malignant neoplasia, particularly cancer, such as e.g. any of those cancer diseases described above.

In the context of their properties, functions and usabilities mentioned herein, the (E)-N-(2-amino-phenyl)-3-{1-[4-(1-methyl-1H-pyrazol-4-yl)-benzenesulfonyl]-1H-pyrrol-3-yl}-acrylamide salts according to the present invention are expected to be distinguished by valuable and desirable effects related therewith, such as e.g. by low toxicity, superior bioavailability in general (such as e.g. good enteral absorption), superior therapeutic window, absence of significant side effects, and/or further beneficial effects related with their therapeutic and pharmaceutical suitability (e.g. solubility behaviour).

The present invention further includes a method for the treatment of mammals, including humans, which are suffering from one of the abovementioned conditions, illnesses, disorders or diseases. The method comprises that a pharmacologically active and therapeutically effective and tolerable amount of one or more of the (E)-N-(2-amino-phenyl)-3-{1-[4-(1-methyl-1H-pyrazol-4-yl)-benzenesulfonyl]-1H-pyrrol-3-yl}-acrylamide salts according to this invention, which function by inhibiting histone deacetylases and—in general—by modulating protein acetylation, inducing various cellular effects, in particular induction or repression of gene expression, arresting cell proliferation, inducing cell differentiation and/or inducing apoptosis, is administered to the subject in need of such treatment.

The invention further includes a method for treating diseases and/or disorders responsive or sensitive to the inhibition of histone deacetylases, particularly those diseases mentioned above, such as e.g. cellular neoplasia or diseases different to cellular neoplasia as indicated above, in mammals, including humans, suffering therefrom comprising administering to said mammals in need thereof a pharmacologically active and therapeutically effective and tolerable amount of one or more of the (E)-N-(2-amino-phenyl)-3-{1-[4-(1-methyl-1H-pyrazol-4-yl)-benzenesulfonyl]-1H-pyrrol-3-yl}-acrylamide salts according to the present invention.

The present invention further includes a therapeutic method useful to modulate protein acetylation, gene expression, cell proliferation, cell differentiation and/or apoptosis in vivo in diseases mentioned above, in particular cancer, comprising administering to a subject in need of such therapy a pharmacologically active and therapeutically effective and tolerable amount of one or more of the (E)-N-(2-amino-phenyl)-3-{1-[4-(1-methyl-1H-pyrazol-4-yl)-benzenesulfonyl]-1H-pyrrol-3-yl}-acrylamide salts according to this invention, which function by inhibiting histone deacetylases.

The present invention further provides a method for regulating endogenous or heterologous promotor activity by contacting a cell with a (E)-N-(2-amino-phenyl)-3-{1-[4-(1-methyl-1H-pyrazol-4-yl)-benzenesulfonyl]-1H-pyrrol-3-yl}-acrylamide salt according to this invention.

The invention further relates to the use of the (E)-N-(2-amino-phenyl)-3-{1-[4-(1-methyl-1H-pyrazol-4-yl)-benzenesulfonyl]-1H-pyrrol-3-yl}-acrylamide salts according to the present invention for the production of pharmaceutical compositions which are employed for the treatment and/or prophylaxis and/or amelioration of the diseases, disorders, illnesses and/or conditions as mentioned herein.

The invention further relates to the use of the (E)-N-(2-amino-phenyl)-3-{1-[4-(1-methyl-1H-pyrazol-4-yl)-benzenesulfonyl]-1H-pyrrol-3-yl}-acrylamide salts according to the present invention for the production of pharmaceutical compositions which are employed for the treatment and/or prophylaxis of diseases and/or disorders responsive or sensitive to the inhibition of histone deacetylases, particularly those diseases mentioned above, such as e.g. cellular neoplasia or diseases different to cellular neoplasia as indicated above.

The invention further relates to the use of the (E)-N-(2-amino-phenyl)-3-{1-[4-(1-methyl-1H-pyrazol-4-yl)-benzenesulfonyl]-1H-pyrrol-3-yl}-acrylamide salts according to the present invention for the production of pharmaceutical compositions having histone deacetylase inhibitory activity.

The invention further relates to the use of the (E)-N-(2-amino-phenyl)-3-{1-[4-(1-methyl-1H-pyrazol-4-yl)-benzenesulfonyl]-1H-pyrrol-3-yl}-acrylamide salts according to the present invention for the production of pharmaceutical compositions for inhibiting or treating cellular neoplasia, such as benign or malignant neoplasia, e.g. cancer.

The invention further relates to the use of the (E)-N-(2-amino-phenyl)-3-{1-[4-(1-methyl-1H-pyrazol-4-yl)-benzenesulfonyl]-1H-pyrrol-3-yl}-acrylamide salts according to the present invention for the production of pharmaceutical compositions which can be used for treating, preventing or ameliorating of diseases responsive to arresting aberrant cell growth, such as e.g. (hyper)proliferative diseases of benign or malignant behaviour, such as e.g. any of those diseases mentioned herein, particularly cancer, such as e.g. any of those cancer diseases described herein above.

The invention further relates to the use of the (E)-N-(2-ammo-phenyl)-3-{1-[4-(1-methyl-1H-pyrazol-4-yl)-benzenesulfonyl]-1H-pyrrol-3-yl}-acrylamide salts according to the present invention for the production of pharmaceutical compositions which can be used for treating, preventing or ameliorating of disorders responsive to induction of apoptosis, such as e.g. any of those diseases mentioned herein, particularly cancer, such as e.g. any of those cancer diseases described herein above.

The invention further relates to the use of the (E)-N-(2-amino-phenyl)-3-{1-[4-(1-methyl-1H-pyrazol-4-yl)-benzenesulfonyl]-1H-pyrrol-3-yl}acrylamide salts according to the present invention for the production of pharmaceutical compositions which can be used for treating, preventing or ameliorating of disorders responsive to induction of differentiation, such as e.g. any of those diseases mentioned herein, particularly cancer, such as e.g. any of those cancer diseases described herein above.

The invention further relates to the use of the (E)-N-(2-amino-phenyl)-3-{1-[4-(1-methyl-1H-pyrazol-4-yl)-benzenesulfonyl]-1H-pyrrol-3-yl}-acrylamide salts according to the present invention for the production of pharmaceutical compositions which can be used for treating, preventing or ameliorating of benign or malignant neoplasia, particularly cancer, such as e.g. any of those cancer diseases described herein above.

The invention further relates to the use of the (E)-N-(2-amino-phenyl)-3-{1-[4-(1-methyl-1H-pyrazol-4-yl)-benzenesulfonyl]-1H-pyrrol-3-yl}-acrylamide salts according to the present invention for the production of pharmaceutical compositions for the treatment of a disease different to a cellular neoplasia and sensitive to histone deacetylase inhibitor therapy, such as the non-malignant diseases mentioned before.

The invention further relates to the use of the (E)-N-(2-amino-phenyl)-3-{1-[4-(1-methyl-1H-pyrazol-4-yl)-benzenesulfonyl]-1H-pyrrol-3-yl}-acrylamide salts according to the present invention for the production of pharmaceutical compositions for inhibiting histone deacetylase activity in the treatment of diseases responsive to said inhibition or to the functional consequences thereof.

The invention further relates to a method for treating, preventing or ameliorating the diseases, disorders, illnesses and/or conditions mentioned herein in a mammal, in particular a human patient, comprising administering a pharmacologically active and therapeutically effective and tolerable amount of one or more (E)-N-(2-amino-phenyl)-3-{1-[4-(1-methyl-1H-pyrazol-4-yl)-benzenesulfonyl]-1H-pyrrol-3-yl}-acrylamide salts according to the present invention to said mammal in need thereof.

The invention further relates to the (E)-N-(2-amino-phenyl)-3-{1-[4-(1-methyl-1H-pyrazol-4-yl)-benzenesulfonyl]-1H-pyrrol-3-yl}-acrylamide salts according to this invention for use in the treatment and/or prophylaxis of diseases, especially the diseases mentioned.

The invention further relates to pharmaceutical compositions comprising one or more of the (E)-N-(2-amino-phenyl)-3-{1-[4-(1-methyl-1H-pyrazol-4-yl)-benzenesulfonyl]-1H-pyrrol-3-yl}-acrylamide salts according to this invention and a pharmaceutically acceptable carrier or diluent.

The present invention further relates to pharmaceutical compositions comprising one or more of the (E)-N-(2-amino-phenyl)-3-{1-[4-(1H-pyrazol-4-yl)-benzenesulfonyl]-1H-pyrrol-3-yl}-acrylamide salts according to this invention and pharmaceutically acceptable auxiliaries and/or excipients.

The invention further relates to a combination comprising one or more of the (E)-N-(2-amino-phenyl)-3-{1-[4-(1-methyl-1H-pyrazol-4-yl)-benzenesulfonyl]-1H-pyrrol-3-yl}-acrylamide salts according to this invention and a pharmaceutically acceptable diluent, excipient and/or carrier, e.g. for treating, preventing or ameliorating (hyper)proliferative diseases of benign or malignant behaviour and/or disorders responsive to induction of apoptosis, such as, for example, benign or malignant neoplasia, e.g. cancer, such as e.g. any of those cancer diseases described herein above.

The invention further relates to pharmaceutical compositions according to this invention having histone deacetylases inhibitory activity.

The invention further relates to pharmaceutical compositions according to this invention having apoptosis inducing activity.

The invention further relates to pharmaceutical compositions according to this invention having anti-proliferative activity.

The invention further relates to pharmaceutical compositions according to this invention having cell differentiation inducing activity.

The invention further relates to the use of a pharmaceutical composition comprising one or more of the (E)-N-(2-amino-phenyl)-3-{1-[4-(1-methyl-1H-pyrazol-4-yl)-benzenesulfonyl]-1H-pyrrol-3-yl}-acrylamide salts according to this invention and a pharmaceutically acceptable carrier or diluent in the manufacture of a pharmaceutical product, such as e.g. a commercial package, for use in the treatment and/or prophylaxis of the diseases as mentioned.

Additionally, the invention relates to an article of manufacture, which comprises packaging material and a pharmaceutical agent contained within said packaging material, wherein the pharmaceutical agent is therapeutically effective for inhibiting the effects of histone deacetylases, ameliorating the symptoms of an histone deacetylase mediated disorder, and wherein the packaging material comprises a label or package insert which indicates that the pharmaceutical agent is useful for preventing or treating histone deacetylase mediated disorders, and wherein said pharmaceutical agent comprises one or more (E)-N-(2-amino-phenyl)-3-{1-[4-(1-methyl-1H-pyrazol-4-yl)-benzenesulfonyl]-1H-pyrrol-3-yl}-acrylamide salts according to the invention. The packaging material, label and package insert otherwise parallel or resemble what is generally regarded as standard packaging material, labels and package inserts for pharmaceuticals having related utilities.

The pharmaceutical compositions according to this invention are prepared by processes which are known per se and familiar to the person skilled in the art. As pharmaceutical compositions, the (E)-N-(2-amino-phenyl)-3-{1-[4-(1-methyl-1H-pyrazol-4-yl)-benzenesulfonyl]-1H-pyrrol-3-yl}-acrylamide salts of the invention (=active compounds) are either employed as such, or preferably in combination with suitable pharmaceutical auxiliaries and/or excipients, e.g. in the form of tablets, coated tablets, capsules, caplets, suppositories, patches (e.g. as TTS), emulsions, suspensions, gels or solutions, the active compound content advantageously being between 0.1 and 95% and where, by the appropriate choice of the auxiliaries and/or excipients, a pharmaceutical administration form (e.g. a delayed release form or an enteric form) exactly suited to the active compound and/or to the desired onset of action can be achieved.

The person skilled in the art is familiar with auxiliaries, vehicles, excipients, diluents, carriers or adjuvants which are suitable for the desired pharmaceutical formulations, preparations or compositions on account of his/her expert knowledge. In addition to solvents, gel formers, ointment bases and other active compound excipients, for example antioxidants, dispersants, emulsifiers, preservatives, solubilizers, colorants, complexing agents or permeation promoters, can be used.

The administration of the (E)-N-(2-amino-phenyl)-3-{1-[4-(1-methyl-1H-pyrazol-4-yl)-benzenesulfonyl]-1H-pyrrol-3-yl}-acrylamide salts, pharmaceutical compositions or combinations according to the invention may be performed in any of the generally accepted modes of administration available in the art. Illustrative examples of suitable modes of administration include intravenous, oral, nasal, parenteral, topical, transdermal and rectal delivery. Oral and intravenous delivery are preferred.

For the treatment of dermatoses, the (E)-N-(2-amino-phenyl)-3-{1-[4-(1-methyl-1H-pyrazol-4-yl)-benzenesulfonyl]-1H-pyrrol-3-yl}-acrylamide salts according to this invention are in particular administered in the form of those pharmaceutical compositions which are suitable for topical application. For the production of the pharmaceutical compositions, the (E)-N-(2-amino-phenyl)-3-{1-[4-(1-methyl-1H-pyrazol-4-yl)-benzenesulfonyl]-1H-pyrrol-3-yl}-acrylamide salts of the invention (=active compounds) are preferably mixed with suitable pharmaceutical auxiliaries and further processed to give suitable pharmaceutical formulations. Suitable pharmaceutical formulations are, for example, powders, emulsions, suspensions, sprays, oils, ointments, fatty ointments, creams, pastes, gels or solutions.

The pharmaceutical compositions according to the invention are prepared by processes known per se. The dosage of the (E)-N-(2-amino-phenyl)-3-{1-[4-(1-methyl-1H-pyrazol-4-yl)-benzenesulfonyl]-1H-pyrrol-3-yl}-acrylamide salts of the invention (=active compounds) is carried out in the order of magnitude customary for histone deacetylases inhibitors. Topical application forms (such as ointments) for the treatment of dermatoses thus contain the active compounds in a concentration of, for example, 0.1-99%. The customary dose in the case of systemic therapy (p.o.) may be between 0.03 and 60 mg/kg per day, (i. v.) may be between 0.03 and 60 mg/kg/h. In another embodiment, the customary dose in the case of systemic therapy (p.o.) is between 0.3 and 30 mg/kg per day, (i. v.) is between 0.3 and 30 mg/kg/h.

The choice of the optimal dosage regime and duration of medication, particularly the optimal dose and manner of administration of the active compounds necessary in each case can be determined by a person skilled in the art on the basis of his/her expert knowledge.

Depending upon the particular disease, to be treated or prevented, additional therapeutic active agents, which are normally administered to treat or prevent that disease, may optionally be coadministered with the (E)-N-(2-amino-phenyl)-3-{1-[4-(1-methyl-1H-pyrazol-4-yl)-benzenesulfonyl]-1H-pyrrol-3-yl}-acrylamide salts according to the present invention. As used herein, additional therapeutic agents that are normally administered to treat or prevent a particular disease are known as appropriate for the disease being treated.

For example, the (E)-N-(2-amino-phenyl)-3-{1-[4-(1-methyl-1H-pyrazol-4-yl)-benzenesulfonyl]-1H-pyrrol-3-yl}-acrylamide salts according to this invention may be combined with one or more standard therapeutic agents or radiation used for treatment of the diseases as mentioned before.

Thus, in one particular embodiment the (E)-N-(2-amino-phenyl)-3-{1-[4-(1-methyl-1H-pyrazol-4-yl)-benzenesulfonyl]-1H-pyrrol-3-yl}-acrylamide salts according to this invention may be combined with one or more art-known anti-cancer agents, such as e.g. with one or more art-known chemotherapeutic and/or target specific anti-cancer agents as described below, and/or radiation.

Examples of known chemotherapeutic anti-cancer agents frequently used in combination therapy include, but not are limited to (i) alkylating/carbamylating agents such as Cyclophosphamid (Endoxan®), Ifosfamid (Holoxan®), Thiotepa (Thiotepa Lederle®), Melphalan (Alkeran®), or chloroethylnitrosourea (BCNU); (ii) platinum derivatives like cis-platin (Platinex® BMS), oxaliplatin or carboplatin (Cabroplat® BMS); (iii) antimitotic agents/tubulin inhibitors such as vinca alkaloids (vincristine, vinblastine, vinorelbine), taxanes such as Paclitaxel (Taxol®), Docetaxel (Taxotere®) and analogs as well as new formulations and conjugates thereof, epothilones such as Epothilone B (Patupilone®), Azaepothilone (Ixabepilone®) or ZK-EPO, a fully synthetic epothilone B analog; (iv) topoisomerase inhibitors such as anthracyclines (exemplified by Doxorubicin/Adriblastin®), epipodophyllotoxines (exemplified by Etoposide/Etopophos®) and camptothecin and camptothecin analogs (exemplified by Irinotecan/Camptosar® or Topotecan/Hycamtin®); (v) pyrimidine antagonists such as 5-fluorouracil (5-FU), Capecitabine (Xeloda®), Arabinosylcytosine/Cytarabin (Alexan®) or Gemcitabine (Gemzar®); (vi) purin antagonists such as 6-mercaptopurine (Puri-Nethol®), 6-thioguanine or fludarabine (Fludara®) and finally (vii) folic acid antagonists such as methotrexate (Farmitrexat®) or premetrexed (Alimta®).

Examples of target specific anti-cancer drug classes used in experimental or standard cancer therapy include but are not limited to (I) kinase inhibitors such as e.g. Imatinib (Glivec®), ZD-1839/Gefitinib (Iressa®), Bay43-9006 (Sorafenib), SU11248/Sunitinib (Sutent®) or OSI-774/Erlotinib (Tarceva®); (ii) proteasome inhibitors such as PS-341/Bortezumib (Velcade®); (iii) heat shock protein 90 inhibitors like 17-allylaminogeldanamycin (17-AAG); (iv) vascular targeting agents (VTAs) like combretastin A4 phosphate or AVE8062/AC7700 and anti-angiogenic drugs like the VEGF antibodies, such as Bevacizumab (Avastin®), or KDR tyrosine kinase inhibitors such as PTK787/ZK222584 (Vatalanib); (v) monoclonal antibodies such as Trastuzumab (Herceptin®) or Rituximab (MabThera/Rituxan®) or Alemtuzumab (Campath®) or Tositumab (Bexxar®) or C225/Cetuximab (Erbitux®) or Avastin (see above) as well as mutants and conjugates of monoclonal antibodies, e.g. Gemtuzumab ozogamicin (Mylotarg®) or Ibritumomab tiuxetan (Zevalin®), and antibody fragments; as well as mutants and conjugates of monoclonal antibodies and antibody fragments; (vi) oligonucleotide based therapeutics like G-3139/Oblimersen (Genasense®); (vii) Toll-like receptor/TLR 9 agonists like Promune®, TLR 7 agonists like Imiquimod (Aldara®) or Isatoribine and analogues thereof, or TLR 7/8 agonists like Resiquimod as well as immunostimulatory RNA as TLR 7/8 agonists; (viii) protease inhibitors (ix) hormonal therapeutics such as anti-estrogens (e.g. Tamoxifen or Raloxifen), anti-androgens (e.g. Flutamide or Casodex), LHRH analogs (e.g. Leuprolide, Goserelin or Triptorelin) and aromatase inhibitors.

Other known target specific anti-cancer agents which can be used for combination therapy include bleomycin, retinoids such as all-trans retinoic acid (ATRA), DNA methyltransferase inhibitors such as the 2-deoxycytidine derivative Decitabine (Docagen®) and 5-Azacytidine, alanosine, cytokines such as interleukin-2, interferons such as interferon α2 or interferon-γ, death receptor agonists, such as TRAIL, DR4/5 agonistic antibodies, FasL and TNF-R agonists, and finally histone deacetylase inhibitors different to the (E)-N-(2-amino-phenyl)-3-{1-[4-(1-methyl-1H-pyrazol-4-yl)-benzenesulfonyl]-1H-pyrrol-3-yl}-acrylamide salts according to this invention such as SAHA, PXD101, MS275, MGCD0103, Depsipeptide/FK228, NVP-LBH589, NVP-LAQ824, Valproic acid (VPA) and butyrates.

As exemplary anti-cancer agents for use in combination with the (E)-N-(2-amino-phenyl)-3-{1-[4-(1-methyl-1H-pyrazol-4-yl)-benzenesulfonyl]-1H-pyrrol-3-yl}-acrylamide salts according to this invention in the co-therapies mentioned herein any of the following drugs may be mentioned, without being restricted thereto, 5 FU, actinomycin D, ABARELIX, ABCIXIMAB, ACLARUBICIN, ADAPALENE, ALEMTUZUMAB, ALTRETAMINE, AMINOGLUTETHIMIDE, AMIPRILOSE, AMRUBICIN, ANASTROZOLE, ANCITABINE, ARTEMISININ, AZATHIOPRINE, BASILIXIMAB, BENDAMUSTINE, BEVACIZUMAB, BEXXAR, BICALUTAMIDE, BLEOMYCIN, BORTEZOMIB, BROXURIDINE, BUSULFAN, CAMPATH, CAPECITABINE, CARBOPLATIN, CARBOQUONE, CARMUSTINE, CETRORELIX, CHLORAMBUCIL, CHLORMETHINE, CISPLATIN, CLADRIBINE, CLOMIFENE, CYCLOPHOSPHAMIDE, DACARBAZINE, DACLIZUMAB, DACTINOMYCIN, DAUNORUBICIN, DECITABINE, DESLORELIN, DEXRAZOXANE, DOCETAXEL, DOXIFLURIDINE, DOXORUBICIN, DROLOXIFENE, DROSTANOLONE, EDELFOSINE, EFLORNITHINE, EMITEFUR, EPIRUBICIN, EPITIOSTANOL, EPTAPLATIN, ERBITUX, ERLOTINIB, ESTRAMUSTINE, ETOPOSIDE, EXEMESTANE, FADROZOLE, FINASTERIDE, FLOXURIDINE, FLUCYTOSINE, FLUDARABINE, FLUOROURACIL, FLUTAMIDE, FORMESTANE, FOSCARNET, FOSFESTROL, FOTEMUSTINE, FULVESTRANT, GEFITINIB, GENASENSE, GEMCITABINE, GLIVEC, GOSERELIN, GUSPERIMUS, HERCEPTIN, IDARUBICIN, IDOXURIDINE, IFOSFAMIDE, IMATINIB, IMPROSULFAN, INFLIXIMAB, IRINOTECAN, IXABEPILONE, LANREOTIDE, LETROZOLE, LEUPRORELIN, LOBAPLATIN, LOMUSTINE, LUPROLIDE, MELPHALAN, MERCAPTOPURINE, METHOTREXATE, METUREDEPA, MIBOPLATIN, MIFEPRISTONE, MILTEFOSINE, MIRIMOSTIM, MITOGUAZONE, MITOLACTOL, MITOMYCIN, MITOXANTRONE, MIZORIBINE, MOTEXAFIN, MYLOTARG, NARTOGRASTIM, NEBAZUMAB, NEDAPLATIN, NILUTAMIDE, NIMUSTINE, OCTREOTIDE, ORMELOXIFENE, OXALIPLATIN, PACLITAXEL, PALIVIZUMAB, PATUPILONE, PEGASPARGASE, PEGFILGRASTIM, PEMETREXED, PENTETREOTIDE, PENTOSTATIN, PERFOSFAMIDE, PIPOSULFAN, PIRARUBICIN, PLICAMYCIN, PREDNIMUSTINE, PROCARBAZINE, PROPAGERMANIUM, PROSPIDIUM CHLORIDE, RALOXIFEN, RALTITREXED, RANIMUSTINE, RANPIRNASE, RASBURICASE, RAZOXANE, RITUXIMAB, RIFAMPICIN, RITROSULFAN, ROMURTIDE, RUBOXISTAURIN, SARGRAMOSTIM, SATRAPLATIN, SIROLIMUS, SOBUZOXANE, SORAFENIB, SPIROMUSTINE, STREPTOZOCIN, SUNITINIB, TAMOXIFEN, TASONERMIN, TEGAFUR, TEMOPORFIN, TEMOZOLOMIDE, TENIPOSIDE, TESTOLACTONE, THIOTEPA, THYMALFASIN, TIAMIPRINE, TOPOTECAN, TOREMIFENE, TRAIL, TRASTUZUMAB, TREOSULFAN, TRIAZIQUONE, TRIMETREXATE, TRIPTORELIN, TROFOSFAMIDE, UREDEPA, VALRUBICIN, VATALANIB, VERTEPORFIN, VINBLASTINE, VINCRISTINE, VINDESINE, VINORELBINE, VOROZOLE and ZEVALIN.

The anti-cancer agents mentioned herein above as combination partners of the (E)-N-(2-amino-phenyl)-3-{1-[4-(1-methyl-1H-pyrazol-4-yl)-benzenesulfonyl]-1H-pyrrol-3-yl}-acrylamide salts according to this invention are meant to include pharmaceutically acceptable derivatives thereof, such as e.g. their pharmaceutically acceptable salts.

The person skilled in the art is aware on the base of his/her expert knowledge of the kind, total daily dosage(s) and administration form(s) of the additional therapeutic agent(s) coadministered. Said total daily dosage(s) can vary within a wide range.

In practicing the present invention and depending on the details, characteristics or purposes of their uses mentioned above, the (E)-N-(2-amino-phenyl)-3-{1-[4-(1-methyl-1H-pyrazol-4-yl)-benzenesulfonyl]-1H-pyrrol-3-yl}-acrylamide salts according to the present invention may be administered in combination therapy separately, sequentially, simultaneously, concurrently or chronologically staggered (such as e.g. as combined unit dosage forms, as separate unit dosage forms, as adjacent discrete unit dosage forms, as fixed or non-fixed combinations, as kit-of-parts or as admixtures) with one or more standard therapeutics, in particular, art-known anti-cancer agents (chemotherapeutic and/or target specific anti-cancer agents), such as e.g. any of those mentioned above.

In this context, the present invention further relates to a combination comprising a first active ingredient, which is at least one (E)-N-(2-amino-phenyl)-3-{1-[4-(1-methyl-1H-pyrazol-4-yl)-benzenesulfonyl]-1H-pyrrol-3-yl}-acrylamide salt according to this invention, and a second active ingredient, which is at least one art-known standard therapeutic, for example an art-known anti-cancer agent, such as e.g. one or more of those mentioned herein above, for separate, sequential, simultaneous, concurrent or chronologically staggered use in therapy, such as e.g. in therapy of any of those diseases mentioned herein.

The term "combination" according to this invention may be present as a fixed combination, a non-fixed combination or a kit-of-parts.

A "fixed combination" is defined as a combination wherein the said first active ingredient and the said second active ingredient are present together in one unit dosage or in a single entity. One example of a "fixed combination" is a pharmaceutical composition wherein the said first active ingredient and the said second active ingredient are present in admixture for simultaneous administration, such as in a formulation. Another example of a "fixed combination" is a pharmaceutical combination wherein the said first active ingredient and the said second active ingredient are present in one unit without being in admixture.

A "kit-of-parts" is defined as a combination wherein the said first active ingredient and the said second active ingredient are present in more than one unit. One example of a "kit-of-parts" is a combination wherein the said first active ingredient and the said second active ingredient are present separately. The components of the kit-of-parts may be administered separately, sequentially, simultaneously, concurrently or chronologically staggered.

The present invention further relates to a pharmaceutical composition comprising a first active ingredient, which is at least one (E)-N-(2-amino-phenyl)-3-{1-[4-(1-methyl-1H-pyrazol-4-yl)-benzenesulfonyl]-1H-pyrrol-3-yl}-acrylamide salt according to this invention, and a second active ingredient, which is at least one art-known anti-cancer agent, such as e.g. one or more of those mentioned herein above, and, optionally, a pharmaceutically acceptable carrier or diluent, for separate, sequential, simultaneous, concurrent or chronologically staggered use in therapy, such as e.g. in therapy of diseases responsive or sensitive to the inhibition of histone deacetylases, particularly (hyper)proliferative diseases and/or disorders responsive to induction of apoptosis, such as e.g. any of those diseases mentioned herein, like benign or malignant neoplasia, especially cancer, particularly any of those cancer diseases described above.

The present invention further relates to a combination product comprising a.) at least one (E)-N-(2-amino-phenyl)-3-{1-[4-(1-methyl-1H-pyrazol-4-yl)-benzenesulfonyl]-1H-pyrrol-3-yl}-acrylamide salt according to this invention formulated with a pharmaceutically acceptable carrier or diluent, and b.) at least one art-known anti-cancer agent, such as e.g. one or more of those mentioned herein above, formulated with a pharmaceutically acceptable carrier or diluent.

The present invention further relates to a kit-of-parts comprising a preparation of a first active ingredient, which is a (E)-N-(2-amino-phenyl)-3-{1-[4-(1-methyl-1H-pyrazol-4-yl)-benzenesulfonyl]-1H-pyrrol-3-yl}-acrylamide salt according to this invention, and a pharmaceutically acceptable carrier or diluent; a preparation of a second active ingredient, which is an art-known anti-cancer agent, such as one of those mentioned above, and a pharmaceutically acceptable carrier or diluent; for simultaneous, concurrent, sequential, separate or chronologically staggered use in therapy. Optionally, said kit comprises instructions for its use in therapy, e.g. to treat diseases responsive or sensitive to the inhibition of histone deacetylases, such as e.g. cellular neoplasia or diseases different to cellular neoplasia as indicated above, particularly cancer, such as e.g. any of those cancer diseases described above.

The present invention further relates to a combined preparation comprising at least one (E)-N-(2-amino-phenyl)-3-{1-[4-(1-methyl-1H-pyrazol-4-yl)-benzenesulfonyl]-1H-pyrrol-3-yl}-acrylamide salt according to this invention and at least one art-known anti-cancer agent for simultaneous, concurrent, sequential or separate administration.

In this connection, the present invention further relates to combinations, compositions, formulations, preparations or kits according to the present invention having histone deacetylases inhibitory activity.

Also in this connection, the present invention further relates to combinations, compositions, formulations, preparations or kits according to the present invention having anti-(hyper)proliferative and/or apoptosis inducing activity.

In addition, the present invention further relates to a method for treating in combination therapy diseases responsive or sensitive to the inhibition of histone deacetylases, such as e.g. those mentioned above, e.g. (hyper)proliferative diseases and/or disorders responsive to induction of apoptosis, like cancer, in a patient comprising administering a combination, composition, formulation, preparation or kit as described herein to said patient in need thereof.

In addition, the present invention further relates to a method for treating diseases responsive or sensitive to the inhibition of histone deacetylases, such as e.g. cancer, in a patient comprising administering in combination therapy separately, simultaneously, concurrently, sequentially or chronologically staggered a pharmaceutically active and therapeutically effective and tolerable amount of a pharmaceutical composition, which comprises a (E)-N-(2-amino-phenyl)-3-{1-[4-(1-methyl-1H-pyrazol-4-yl)-benzenesulfonyl]-1H-pyrrol-3-yl}-acrylamide salt according to this invention and a pharmaceutically acceptable carrier or diluent, and a pharmaceutically active and therapeutically effective and tolerable amount of one or more art-known anti-cancer agents, such as e.g. one or more of those mentioned herein, to said patient in need thereof.

In further addition, the present invention relates to a method for treating, preventing or ameliorating (hyper)proliferative diseases and/or disorders responsive to induction of apoptosis, such as e.g. benign or malignant neoplasia, e.g. cancer, particularly any of those cancer diseases mentioned herein, in a patient comprising administering separately, simultaneously, concurrently, sequentially or chronologically staggered to said patient in need thereof an amount of a first active compound, which is a (E)-N-(2-amino-phenyl)-3-{1-[4-(1-methyl-H-pyrazol-4-yl)-benzenesulfonyl]-1H-pyrrol-3-yl}-acrylamide salt according to the present invention, and an amount of at least one second active compound, said at least one second active compound being a standard therapeutic agent, particularly at least one art-known anti-cancer agent, such as e.g. one or more of those chemotherapeutic and target-specific anti-cancer agents mentioned herein, wherein the amounts of the first active compound and said second active compound result in a therapeutic effect.

In yet further addition, the present invention relates to a method for treating, preventing or ameliorating (hyper)proliferative diseases and/or disorders responsive to induction of apoptosis, such as e.g. benign or malignant neoplasia, e.g. cancer, particularly any of those cancer diseases mentioned herein, in a patient comprising administering a combination according to the present invention.

In addition, the present invention further relates to the use of a composition, combination, formulation, preparation or kit according to this invention in the manufacture of a pharmaceutical product, such as e.g. a commercial package or a medicament, for treating, preventing, or ameliorating diseases responsive or sensitive to the inhibition of histone deacetylases, particularly those diseases mentioned herein, such as e.g. benign or malignant neoplasia, particularly cancer.

The present invention further relates to a commercial package comprising one or more (E)-N-(2-amino-phenyl)-3-{1-[4-(1-methyl-1H-pyrazol-4-yl)-benzenesulfonyl]-1H-pyrrol-3-yl}-acrylamide salts of the present invention together with instructions for simultaneous, concurrent, sequential or separate use with one or more chemotherapeutic and/or target specific anti-cancer agents, such as e.g. any of those mentioned herein.

The present invention further relates to a commercial package consisting essentially of one or more (E)-N-(2-amino-phenyl)-3-{1-[4-(1-methyl-1H-pyrazol-4-yl)-benzenesulfonyl]-1H-pyrrol-3-yl}-acrylamide salts of the present invention as sole active ingredient together with instructions for simultaneous, concurrent, sequential or separate use with one or more chemotherapeutic and/or target specific anti-cancer agents, such as e.g. any of those mentioned herein.

The present invention further relates to a commercial package comprising one or more chemotherapeutic and/or target specific anti-cancer agents, such as e.g. any of those mentioned herein, together with instructions for simultaneous, concurrent, sequential or separate use with one or more (E)-N-(2-amino-phenyl)-3-{1-[4-(1-methyl-1H-pyrazol-4-yl)-benzenesulfonyl]-1H-pyrrol-3-yl}-acrylamide salts according to the present invention.

The compositions, combinations, preparations, formulations, kits or packages mentioned in the context of the combination therapy according to this invention may also include more than one of the (E)-N-(2-amino-phenyl)-3-{1-[4-(1-methyl-1H-pyrazol-4-yl)-benzenesulfonyl]-1H-pyrrol-3-yl}-acrylamide salts according to this invention and/or more than one of the art-known anti-cancer agents mentioned.

The first and second active ingredient of a combination or kit-of-parts according to this invention may be provided as separate formulations (i.e. independently of one another), which are subsequently brought together for simultaneous, sequential, separate or chronologically staggered use in combination therapy; or packaged and presented together as separate components of a combination pack for simultaneous, concurrent, sequential, separate or chronologically staggered use in combination therapy.

The type of pharmaceutical formulation of the first and second active ingredient of a combination or kit-of-parts according to this invention can be similar, i.e. both ingredients are formulated in separate tablets or capsules, or can be different, i.e. suited for different administration forms, such as e.g. one active ingredient is formulated as tablet or capsule and the other is formulated for e.g. intravenous administration.

The amounts of the first and second active ingredients of the combinations, compositions or kits according to this invention may together comprise a therapeutically effective amount for the treatment, prophylaxis or amelioration of a disease responsive or sensitive the inhibition of histone deacetylases, such as, for example, one of those diseases mentioned herein, e.g. benign or malignant neoplasia, particularly cancer, like any one of those cancer diseases mentioned herein.

In addition, the (E)-N-(2-amino-phenyl)-3-{1-[4-(1-methyl-1H-pyrazol-4-yl)-benzenesulfonyl]-1H-pyrrol-3-yl}-acrylamide salts according to the present invention can be used in the pre- or post-surgical treatment of cancer.

In further addition, the (E)-N-(2-amino-phenyl)-3-{1-[4-(1-methyl-1H-pyrazol-4-yl)-benzenesulfonyl]-1H-pyrrol-3-yl}-acrylamide salts according to the present invention can be used in combination with radiation therapy, in particular in sensitization of cancer patients towards standard radiation therapy.

A combination according to this invention can refer to a composition comprising both the (E)-N-(2-amino-phenyl)-3-{1-[4-(1-methyl-1H-pyrazol-4-yl)-benzenesulfonyl]-1H-pyrrol-3-yl}-acrylamide salt(s) according to this invention and the other active anti-cancer agent(s) in a fixed combination (fixed unit dosage form), or a medicament pack comprising the two or more active ingredients as discrete separate dosage forms (non-fixed combination). In case of a medicament pack comprising the two or more active ingredients, the active ingredients are preferably packed into blister cards which are suited for improving compliance.

Each blister card preferably contains the medicaments to be taken on one day of treatment. If the medicaments are to be taken at different times of day, the medicaments can be disposed in different sections on the blister card according to the different ranges of times of day at which the medicaments are to be taken (for example morning and evening or morning, midday and evening). The blister cavities for the medicaments to be taken together at a particular time of day are accommodated in the respective range of times of day. The various times of day are, of course, also put on the blister in a clearly visible way. It is also possible, of course, for example to indicate a period in which the medicaments are to be taken, for example stating the times.

The daily sections may represent one line of the blister card, and the times of day are then identified in chronological sequence in this column.

Medicaments which must be taken together at a particular time of day are placed together at the appropriate time on the blister card, preferably a narrow distance apart, allowing them to be pushed out of the blister easily, and having the effect that removal of the dosage form from the blister is not forgotten.

The invention claimed is:

1. A salt of (E)-N-(2-amino-phenyl)-3-{1-[4-(1-methyl-1H-pyrazol-4-yl)-benzenesulfonyl]-1H-pyrrol-3-yl}-acrylamide, which is a besylate, tosylate or 2-naphtylsulfonate salt of (E)-N-(2-amino-phenyl)-3-{1-[4-(1-methyl-1H-pyrazol-4-yl)-benzenesulfonyl]-1H-pyrrol-3-yl}-acrylamide.

2. A pharmaceutical composition comprising a (E)-N-(2-amino-phenyl)-3-{1-[4-(1-methyl-1H-pyrazol-4-yl)-benzenesulfonyl]-1H-pyrrol-3-yl}-acrylamide salt according to claim 1 and one or more pharmaceutically acceptable excipients, diluents and/or carriers.

3. A pharmaceutical composition comprising a hydrobromide, methansulfonate, hemi ethane-1,2-disulfonate, benzenesulfonate, toluenesulfonate or 2-naphthalenesulfonate salt of (E)-N-(2-amino-phenyl)-3-{1-[4-(1-methyl-1H-pyrazol-4-yl)-benzenesulfonyl]-1H-pyrrol-3-yl}-acrylamide and one or more pharmaceutically acceptable excipients, diluents and/or carriers.

4. A mesylate salt of (E)-N-(2-amino-phenyl)-3-{1-[4-(1-methyl-1H-pyrazol-4-yl)-benzenesulfonyl]-1H-pyrrol-3-yl}-acrylamide in its polymorphic form A, which has powder X-ray diffraction peaks at: 3.9, 16.4 and 16.9±0.1 (°2θ);
or
a hemi ethane-1,2-disulfonate salt of (E)-N-(2-amino-phenyl)-3-{1-[4-(1-methyl-1H-pyrazol-4-yl)-benzenesulfonyl]-1H-pyrrol-3-yl}-acrylamide in its polymorphic form A, which has powder X-ray diffraction peaks at: 16.0, 22.7 and 25.1±0.1 (°2θ);
or
a besylate salt of (E)-N-(2-amino-phenyl)-3-{1-[4-(1-methyl-1H-pyrazol-4-yl)-benzenesulfonyl]-1H-pyrrol-3-yl}-acrylamide in its polymorphic form A, which has powder X-ray diffraction peaks at: 19.1, 20.4 and 22.7±0.1 (°2θ);
or
a toluenesulfonate salt of (E)-N-(2-amino-phenyl)-3-{1-[4-(1-methyl-1H-pyrazol-4-yl)-benzenesulfonyl]-1H-pyrrol-3-yl}-acrylamide in one of the following polymorphic forms:
polymorphic form A, which has powder X-ray diffraction peaks at: 7.0, 19.6 and 19.9±0.1 (°2θ);
polymorphic form B, which has powder X-ray diffraction peaks at: 18.1, 21.2 and 22.9±0.1 (°2θ);
polymorphic form C; which has powder X-ray diffraction peaks at: 8.9, 11.7 and 20.3±0.1 (°2θ);
polymorphic form D, which has powder X-ray diffraction peaks at: 17.1, 18.7 and 22.5±0.1 (°2θ);
polymorphic form E, which has powder X-ray diffraction peaks at: 6.9, 13.0 and 19.8±0.1 (°2θ);
polymorphic form F, which has powder X-ray diffraction peaks at: 5.3, 10.5 and 18.6+0.1 (°2θ);
polymorphic form G, which has powder X-ray diffraction peaks at: 6.6, 19.2 and 20.4±0.1 (°2θ); or
polymorphic form H, which has powder X-ray diffraction peaks at: 6.7, 19.5 and 19.8±0.1 (°2θ);
or
a 2-naphtylsulfonate salt of (E)-N-(2-amino-phenyl)-3-{1-[4-(1-methyl-1H-pyrazol-4-yl)-benzenesulfonyl]-1H-pyrrol-3-yl}-acrylamide in one of the following polymorphic forms:
polymorphic form A+B, which has powder X-ray diffraction peaks at: 4.6, 18.5 and 23.8 ±0.1 (°2θ);
polymorphic form A+B, which has powder X-ray diffraction peaks at: 4.7, 6.8 and 18.5 ±0.1 (°2θ); or
polymorphic form C, which has powder X-ray diffraction peaks at: 5.8, 17.3 and 22.9±0.1 (°2θ).

5. The mesylate salt of (E)-N-(2-amino-phenyl)-3-{1-[4-(1-methyl-1H-pyrazol-4-yl)-benzenesulfonyl]-1H-pyrrol-3-yl}-acrylamide according to claim 4 in its polymorphic form A, which has powder X-ray diffraction peaks at: 3.9, 16.4 and 16.9±0.1 (°2θ).

6. The hemi ethane-1,2-disulfonate salt of (E)-N-(2-amino-phenyl)-3-{1-[4-(1-methyl-1H-pyrazol-4-yl)-benzenesulfonyl]-1H-pyrrol-3-yl}-acrylamide according to claim 4 in its polymorphic form A, which has powder X-ray diffraction peaks at: 16.0, 22.7 and 25.1±0.1 (°2θ).

7. The besylate salt of (E)-N-(2-amino-phenyl)-3-{1-[4-(1-methyl-1H-pyrazol-4-yl)-benzenesulfonyl]-1H-pyrrol-3-yl}-acrylamide according to claim 4 in its polymorphic form A, which has powder X-ray diffraction peaks at: 19.1, 20.4 and 22.7±0.1 (°2θ).

8. The toluenesulfonate salt of (E)-N-(2-amino-phenyl)-3-{1-[4-(1-methyl-1H-pyrazol-4-yl)-benzenesulfonyl]-1H-pyrrol-3-yl}-acrylamide according to claim 4 in one of the following polymorphic forms:
polymorphic form A, which has powder X-ray diffraction peaks at: 7.0, 19.6 and 19.9±0.1 (°2θ);
polymorphic form B, which has powder X-ray diffraction peaks at: 18.1, 21.2 and 22.9±0.1 (°2θ);
polymorphic form C; which has powder X-ray diffraction peaks at: 8.9, 11.7 and 20.3±0.1 (°2θ);
polymorphic form D, which has powder X-ray diffraction peaks at: 17.1, 18.7 and 22.5±0.1 (°2θ);
polymorphic form E, which has powder X-ray diffraction peaks at: 6.9, 13.0 and 19.8±0.1 (°2θ);
polymorphic form F, which has powder X-ray diffraction peaks at: 5.3, 10.5 and 18.6+0.1 (°2θ);
polymorphic form G; which has powder X-ray diffraction peaks at: 6.6, 19.2 and 20.4±0.1 (°2θ); or
polymorphic form H, which has powder X-ray diffraction peaks at: 6.7, 19.5 and 19.8±0.1 (°2θ).

9. The 2-naphtylsulfonate salt of (E)-N-(2-amino-phenyl)-3-{1-[4-(1-methyl-1H-pyrazol-4-yl)-benzenesulfonyl]-1H-pyrrol-3-yl}-acrylamide according to claim 4 in one of the following polymorphic forms:
polymorphic form A+B, which has powder X-ray diffraction peaks at: 4.6, 18.5 and 23.8±0.1 (°2θ);
polymorphic form A+B, which has powder X-ray diffraction peaks at: 4.7, 6.8 and 18.5±0.1 (°2θ); or polymorphic form C, which has powder X-ray diffraction peaks at: 5.8, 17.3 and 22.9±0.1 (°2θ).

10. A method for treating or ameliorating cancer in a patient, comprising administering to said patient a therapeutically effective and tolerable amount of a (E)-N-(2-amino-phenyl)-3-{1-[4-(1-methyl-1H-pyrazol-4-yl)-benzenesulfonyl]-1H-pyrrol-3-yl}-acrylamide salt according to claim 1.

11. A method according to claim 10, wherein said cancer is a solid tumor of the breast, bladder, bone, brain, central or peripheral nervous system, colon, endocrine gland, thyroid or adrenal cortex, esophagus, endometrium, germ cells, head and neck, kidney, liver, lung, larynx or hypopharynx, mesothelioma, ovary, pancreas, prostate, rectum, renal, small intestine, soft tissue, testis, stomach, skin, ureter, vagina or vulva, or a malignant neoplasia, retinoblastoma, or Wilms tumor, or a hematological tumor, leukemia, lymphoma, non-Hodgkins disease, chronic or acute myeloid leukemia, acute lymphoblastic leukemia, Hodgkins disease, multiple myeloma, T-cell lymphoma, myelodysplastic syndrome, plasma cell neoplasia, paraneoplastic syndrome, a cancer of unknown primary site, or an AIDS related malignancy.

12. A method for treating or ameliorating cancer in a patient, comprising administering to said patient a therapeutically effective and tolerable amount of a (E)-N-(2-aminophenyl)-3-{1-[4-(1-methyl-1H-pyrazol-4-yl)-benzenesulfonyl]-1H-pyrrol-3-yl}-acrylamide salt according to claim 4.

13. A method according to claim 12, wherein said cancer is a solid tumor of the breast, bladder, bone, brain, central or peripheral nervous system, colon, endocrine gland, thyroid or adrenal cortex, esophagus, endometrium, germ cells, head and neck, kidney, liver, lung, larynx or hypopharynx, mesothelioma, ovary, pancreas, prostate, rectum, renal, small intestine, soft tissue, testis, stomach, skin, ureter, vagina or vulva, or a malignant neoplasia, retinoblastoma, or Wilms tumor, or a hematological tumor, leukemia, lymphoma, non-Hodgkins disease, chronic or acute myeloid leukemia, acute lymphoblastic leukemia, Hodgkins disease, multiple myeloma, T-cell lymphoma, myelodysplastic syndrome, plasma cell neoplasia, paraneoplastic syndrome, a cancer of unknown primary site, or an AIDS related malignancy.

* * * * *

UNITED STATES PATENT AND TRADEMARK OFFICE
CERTIFICATE OF CORRECTION

PATENT NO. : 8,557,858 B2  Page 1 of 1
APPLICATION NO. : 12/921889
DATED : October 15, 2013
INVENTOR(S) : Volz et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 346 days.

Signed and Sealed this

Fifteenth Day of September, 2015

Michelle K. Lee
*Director of the United States Patent and Trademark Office*